US012743945B2

(12) United States Patent
Nagy et al.

(10) Patent No.: US 12,743,945 B2
(45) Date of Patent: Sep. 22, 2026

(54) WIRELESS PATIENT MONITORING COMPLIANCE SYSTEM

(71) Applicant: Invisalert Solutions, Inc., West Chester, PA (US)

(72) Inventors: Peter A. Nagy, Newtown Square, PA (US); Detlev Ansinn, Doylestown, PA (US)

(73) Assignee: Invisalert Solutions, Inc., West Chester, PA (US)

(*) Notice: Subject to any disclaimer, the term of this patent is extended or adjusted under 35 U.S.C. 154(b) by 131 days.

(21) Appl. No.: 18/806,484

(22) Filed: Aug. 15, 2024

(65) Prior Publication Data

US 2024/0404391 A1 Dec. 5, 2024

Related U.S. Application Data

(63) Continuation of application No. 17/642,464, filed as application No. PCT/US2020/050548 on Sep. 11, 2020, now Pat. No. 12,094,318.

(60) Provisional application No. 62/899,080, filed on Sep. 11, 2019.

(51) Int. Cl.

| | |
|---|---|
| ***G08B 21/18*** | (2006.01) |
| ***A61B 5/00*** | (2006.01) |
| ***A61B 5/11*** | (2006.01) |
| ***G08B 21/02*** | (2006.01) |

(Continued)

(52) U.S. Cl.

CPC ............ *G08B 21/182* (2013.01); *A61B 5/002* (2013.01); *A61B 5/1113* (2013.01); *A61B 5/1118* (2013.01); *A61B 5/4809* (2013.01); *A61B 5/681* (2013.01); *A61B 5/7405* (2013.01); *A61B 5/742* (2013.01); *A61B 5/7455* (2013.01); *G08B 21/0261* (2013.01); *G08B 21/043* (2013.01); *G08B 21/06* (2013.01); *A61B 2503/20* (2013.01); *A61B 2562/0219* (2013.01)

(58) Field of Classification Search

CPC .............. G08B 21/182; G08B 21/0261; G08B 21/043; G08B 21/06; A61B 5/002; A61B 5/1113; A61B 5/1118; A61B 5/4809; A61B 5/681; A61B 5/7405; A61B 5/742; A61B 5/7455; A61B 2503/20; A61B 2562/0219; A61B 5/16; A61B 5/6801

See application file for complete search history.

(56) References Cited

U.S. PATENT DOCUMENTS

| | | | |
|---|---|---|---|
| 706,080 | A | 8/1902 | Mitchell |
| 5,077,666 | A | 12/1991 | Brimm et al. |
| 5,218,344 | A | 6/1993 | Ricketts |

(Continued)

FOREIGN PATENT DOCUMENTS

| | | | |
|---|---|---|---|
| GB | 2426180 | A | 11/2006 |
| GB | 2549099 | A | 10/2017 |

(Continued)

OTHER PUBLICATIONS

Welker; U.S. Appl. No. 18/976,319 entitled "Secure mobile device management," filed Dec. 10, 2024.

(Continued)

*Primary Examiner* — Davetta W Goins
(74) *Attorney, Agent, or Firm* — Shay Glenn LLP

(57) ABSTRACT

Methods and apparatuses (e.g., systems, devices, etc.) for close proximity monitoring of subjects, including in particular at-risk psychiatric subjects.

20 Claims, 11 Drawing Sheets

(51) Int. Cl.
*G08B 21/04* (2006.01)
*G08B 21/06* (2006.01)

(56) References Cited

U.S. PATENT DOCUMENTS 5,298,884 A 3/1994 Gilmore et al.
5,566,427 A 10/1996 Lathrop
5,769,290 A 6/1998 Pestana
5,979,095 A 11/1999 Schneider et al.
6,225,906 B1 5/2001 Shore
6,406,426 B1 6/2002 Reuss et al.
6,693,543 B1 2/2004 Stephenson et al.
D507,798 S 7/2005 Jewitt et al.
6,954,148 B2 10/2005 Pulkkinen et al.
7,154,397 B2 12/2006 Zerhusen et al.
7,242,306 B2 7/2007 Wildman et al.
7,382,247 B2 6/2008 Welch et al.
D577,364 S 9/2008 Flynt et al.
7,450,015 B2 11/2008 Singer et al.
D588,152 S 3/2009 Okada
D588,153 S 3/2009 Okada
7,541,935 B2 6/2009 Dring et al.
7,570,152 B2 8/2009 Smith et al.
D599,363 S 9/2009 Mays
D607,001 S 12/2009 Ording
7,642,290 B2 1/2010 Kaplan
D614,641 S 4/2010 Viegers et al.
7,764,167 B2 7/2010 Reeves et al.
7,825,794 B2 11/2010 Janetis et al.
D643,436 S 8/2011 Lemay
D656,157 S 3/2012 Khan et al.
D656,503 S 3/2012 Brierley et al.
D682,262 S 5/2013 Akana et al.
8,605,094 B1 12/2013 Alfaro et al.
D701,229 S 3/2014 Lee
D701,521 S 3/2014 Kim et al.
D715,820 S 10/2014 Rebstöck
D718,779 S 12/2014 Hang Sik et al.
D720,766 S 1/2015 Mandal et al.
D724,603 S 3/2015 Williams et al.
8,984,436 B1 3/2015 Tseng et al.
9,064,391 B2 6/2015 Vardi et al.
D765,110 S 8/2016 Liang
D789,956 S 6/2017 Ortega et al.
D797,133 S 9/2017 Marcolongo et al.
9,928,713 B2 3/2018 Baczuk et al.
D820,850 S 6/2018 Tekamp et al.
10,410,498 B2 9/2019 Coke et al.
D861,719 S 10/2019 Van Der Molen
D866,586 S 11/2019 Suter et al.
10,482,753 B2 11/2019 Nelson et al.
D873,278 S 1/2020 Nakahara et al.
D875,767 S 2/2020 Farnan et al.
D892,151 S 8/2020 Pontious
D906,359 S 12/2020 Nagy et al.
10,896,590 B2 1/2021 Nagy et al.
11,210,918 B2 12/2021 Nagy et al.
11,682,283 B2 6/2023 Nagy et al.
11,688,265 B1 6/2023 Aquino et al.
12,094,318 B2 * 9/2024 Nagy .................... A61B 5/742
2002/0060630 A1 5/2002 Power
2002/0196147 A1 12/2002 Lau
2004/0010720 A1 1/2004 Singh et al.
2005/0094205 A1 5/2005 Lo et al.
2005/0280546 A1 12/2005 Ganley et al.
2007/0118813 A1 5/2007 Forstall et al.
2007/0129983 A1 6/2007 Scherpbier et al.
2007/0267475 A1 11/2007 Hoglund et al.
2008/0012767 A1 1/2008 Caliri et al.
2008/0015903 A1 1/2008 Rodgers
2008/0027288 A1 1/2008 Renz
2008/0141506 A1 6/2008 Langtry et al.
2009/0019890 A1 1/2009 Kirknoff
2009/0075694 A1 3/2009 Kim et al.
2009/0299827 A1 12/2009 Puri et al.
2010/0026510 A1 2/2010 Kiani et al.
2010/0066541 A1 3/2010 Craine
2010/0090971 A1 4/2010 Choi et al.
2010/0201821 A1 8/2010 Niem et al.
2010/0217618 A1 8/2010 Piccirillo et al.
2010/0249540 A1 9/2010 Lisogurski
2010/0253521 A1 10/2010 Williams, Sr. et al.
2011/0061212 A1 3/2011 Piermayr et al.
2011/0082808 A1 4/2011 Beykpour et al.
2011/0105854 A1 5/2011 Kiani et al.
2011/0109461 A1 5/2011 Aninye
2011/0179387 A1 7/2011 Shaffer et al.
2011/0191124 A1 8/2011 Sung et al.
2011/0197163 A1 8/2011 Jegal et al.
2012/0016691 A1 1/2012 Sievenpiper et al.
2012/0095822 A1 4/2012 Chiocchi
2012/0130730 A1 5/2012 Setlur et al.
2012/0154582 A1 6/2012 Johnson et al.
2012/0184207 A1 7/2012 Gaines et al.
2013/0018673 A1 1/2013 Rubin
2013/0097824 A1 4/2013 Chadwick
2013/0110565 A1 5/2013 Means, Jr. et al.
2013/0132908 A1 5/2013 Lee et al.
2013/0145663 A1 6/2013 Greer
2013/0218583 A1 8/2013 Marcolongo et al.
2013/0226607 A1 8/2013 Woody et al.
2013/0227486 A1 8/2013 Brinda
2013/0234853 A1 9/2013 Kazerouni
2014/0067770 A1 3/2014 Cheong et al.
2014/0184408 A1 7/2014 Herbst et al.
2014/0189608 A1 7/2014 Shuttleworth et al.
2014/0222462 A1 8/2014 Shakil et al.
2014/0274115 A1 9/2014 Michalson et al.
2014/0283142 A1 9/2014 Shepherd et al.
2015/0084769 A1 3/2015 Messier et al.
2015/0154379 A1 6/2015 Cvijanovich et al.
2015/0170504 A1 6/2015 Jooste
2015/0242665 A1 8/2015 Antonescu et al.
2015/0264647 A1 9/2015 Lacatus et al.
2016/0026837 A1 1/2016 Good et al.
2016/0078752 A1 3/2016 Vardi
2016/0109853 A1 4/2016 Kobayashi
2016/0239778 A1 8/2016 Suneja
2016/0253470 A1 9/2016 Marcolongo et al.
2017/0032093 A1 2/2017 Norton et al.
2017/0116560 A1 4/2017 Wickstrom et al.
2017/0224063 A1 8/2017 Chadwick
2017/0243056 A1 8/2017 Cheng et al.
2017/0243469 A1 8/2017 Vega et al.
2018/0041944 A1 2/2018 Korneluk et al.
2018/0065248 A1 3/2018 Barral
2018/0165937 A1 6/2018 Devdas et al.
2018/0233225 A1 8/2018 Experton et al.
2018/0369039 A1 12/2018 Bhimavarapu et al.
2019/0034592 A1 1/2019 Gupta et al.
2019/0043337 A1 2/2019 Liu et al.
2019/0146550 A1 5/2019 Berardinelli
2019/0320898 A1 10/2019 Dirghangi et al.
2020/0074099 A1 3/2020 Felice-Steele et al.
2020/0137357 A1 4/2020 Kapoustin et al.
2020/0201260 A1 6/2020 Rodriguez et al.
2020/0357502 A1 11/2020 Lee et al.
2021/0125709 A1 4/2021 Qian et al.
2021/0287783 A1 9/2021 Jhaveri
2022/0189644 A9 6/2022 Barnes et al.
2022/0240779 A1 8/2022 Peyman
2022/0301407 A1 9/2022 Nagy et al.
2023/0019901 A1 1/2023 Muhsin et al.

(56) References Cited

U.S. PATENT DOCUMENTS

| | | | |
|---|---|---|---|
| 2024/0046768 | A1 | 2/2024 | Nagy et al. |
| 2025/0140096 | A1 | 5/2025 | Nagy et al. |

FOREIGN PATENT DOCUMENTS

| | | | |
|---|---|---|---|
| KR | 10-1515597 | B1 | 4/2015 |
| WO | WO02/082348 | A2 | 10/2002 |
| WO | WO2016/102506 | A1 | 6/2016 |

OTHER PUBLICATIONS

Nagy et al.; U.S. Appl. No. 18/955,963 entitled "Apparatus and method for monitoring compliance with patient care protocols" filed Nov. 21, 2024.

Consumer Cellular; Huawei 8652—managing contacts; 1 page (Screenshot); retrieved from the internet (https://www.youtube.com/watch?v=oCazslu6NLg on Sep. 17, 2012.

Contacts Like Listview: Contacts like listview—stack overflow; 1 page; retrieved from the internet (http://stackoverflow.com/questions/5017080/contacts-like-listview) on Feb. 16, 2011.

invisalertsolutions.com; 15-minute checks psychiatry inpatient setting; Feb. 16, 2018; 2 pages retrived from the internet (https://www.invisalertsolutions.com/>(year:2018); on Aug. 18, 2020.

Google Drive Blog; Rapid wireframe sketching in google docs; 2pages; retrived from the internet (https://drive.googleblog.com/2010/05/rapid-wireframe-sketching-in-google-docs.htm) on May 2010.

Java; How to add my app icon in contact list of users' android phone—stack overflow; 1 pages retrieved from the internet (https:stackoverflow.com/questions/25029855/how-to-add-my-app-icon-in-contact-list-of-users-android-phone) on Aug. 18, 2020.

McNickle; 7 E-Health tools to get patients engaged; 5 pages; retrieved from the internet (http://www.informationweek.com/healthcare/patient-tools/7-e-health-tools-to-get-patients-engaged/d/d-id/1106716) on Oct. 8, 2012.

Pandey; [How-to] Backup your phone contacts to google; 1 page (Screenshot); retrieved from the interent (http://www.youtube.com/watch?v=vZwvc-7CCf4) on Nov. 15, 2012.

Sain Lukes College on Google Play Reviews; Similar play app stats; 1 page; retrived from the internet (https://www.similarplay.com/dublabs/saint_lukes_college/apps/com.dud.app.saintlukes) on Aug. 18, 2020.

Vladleevideo; Quick Contacts for Android, 2 pages (Screenshot); retrieved from the internet (https://www.youtube.com/watch?v=iRn97Neh-cY) on Apr. 18, 2017.

Winarno; How to backup contacts on samsung S4; 1 page (Screenshot); retrieved from the internet (https://www.youtube.com/watch?v=_MN9RbuV9Vc>); on Jul. 7, 2014.

Marcolongo et al.; U.S. Appl. No. 29/550,879, entitled "Graphical user interface for display screen or portion thereof," filed Jan. 7, 2016.

Albert et al.; U.S. Appl. No. 18/686,348 entitled "Tamper-resistant wearable band," filed Feb. 23, 2024.

Nagy; U.S. Appl. No. 18/705,441 entitled "Method and apparatus for preventing elopement," filed Apr. 26, 2024.

Nagy; U.S. Appl. No. 18/826,171 entitled "Patient safety monitoring method and apparatus," filed Sep. 5, 2024.

Banja; Preventing sexual attacks in healthcare facilities: Risk management considerations. Journal of healthcare risk management; 33(3); pp. 5-12; Feb. 2014.

* cited by examiner

FIG. 4B
09:52 AM
Log In
Smith, John
Wi-Fi Status
ObservSMART
OBSERVATION COMPLIANCE SAFETY.
OBSERVSMART 1:1 MODULE
Select Unit
Adolescent
Continue
2

WIRELESS PATIENT MONITORING COMPLIANCE SYSTEM

CROSS REFERENCE TO RELATED APPLICATIONS

This patent application is a continuation of U.S. patent application Ser. No. 17/642,464, filed on Mar. 11, 2022, titled "WIRELESS PATIENT MONITORING COMPLIANCE SYSTEM," now U.S. Pat. No. 12,094,318, which is a 371 of International Patent Application No. PCT/US2020/050548, filed on Sep. 11, 2020, titled "WIRELESS PATIENT MONITORING COMPLIANCE SYSTEM," which claims priority to U.S. Provisional Patent Application No. 62/899,080, filed on Sep. 11, 2019, titled "WIRELESS PATIENT MONITORING COMPLIANCE SYSTEM," each of which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Methods and apparatuses (e.g., systems, devices, etc.) for close proximity monitoring of subjects, including in particular at-risk psychiatric subjects.

BACKGROUND

Close monitoring of subjects (e.g., patients such as psychiatric patients) may be necessary to ensure the safety and wellbeing of the subject. For example, settings in healthcare, corrections, schools, and elder care may require closely monitor a subject to ensure their safety. Subject monitoring may be required by order of a physician or by regulatory requirement. For example, psychiatric subjects are routinely placed under 1:1, Line-of-Sight, or other close proximity monitoring protocol. Such subjects may be present in psychiatric hospitals, emergency departments, medical hospitals, corrections, special needs and residential care.

When a subject is placed under close proximity monitoring (e.g., 1:1 monitoring), the observer and subject must be within very close proximity such as "arms-length". The intention is for the observer to constantly monitor the subject, e.g., to prevent suicide or self-harm, elopement, eating disorders or other adverse events. As used herein a subject may be a patient; subjects may be human subjects or non-human (e.g., primate) subjects. The subject's may be prisoners or subjects within a correctional facility.

Under current practice, the observer sits close to the subject but there typically no effective way to ensure compliance for the observer staying within the required proximity of the subject, and/or staying awake and attentive to the subject. It is well documented that subjects under 1:1 monitoring do experience self-harm or other adverse events because of failures in the current practice, which does not provide effective real-time monitoring compliance. Observers may wander away, fall asleep, and/or get distracted, which may enable subjects to commit self-harm. This problem is critically important because subjects in a 1:1 observation are perceived to be at very high or acute risk.

Described herein are apparatuses (e.g., systems, devices, etc.) and methods, including methods of using these systems, that may address these problems.

SUMMARY OF THE DISCLOSURE

In general, described herein are methods and apparatuses (e.g., systems, devices, etc.) for close proximity monitoring of subjects. In particular, described herein are methods and apparatuses to assist an observer in close proximity monitoring of a subject that enhance real-time compliance.

As used herein, an observer may refer to an individual, such as a minder, nurse, caregiver, etc. The observer may be trained or untrained, and may generally be responsible for ongoing monitoring of one (or in some cases as indicated herein, more than one) subject. The observer may be responsible for observing the subject to determine and/or confirm the ongoing status of the subject, e.g., awake/asleep, agitation state (calm, agitated, etc.), or the like.

Close proximity monitoring may generally refer to one-to-one, e.g., one observer to one subject, monitoring. Close proximity monitoring may include a range (e.g., distance between the subject and the observer) that may be defined (e.g., 5 feet or less, 7 feet or less, 10 feet or less, 15 feet or less, 20 feet or less, 25 feet or less, etc.). Close proximity reporting may include ongoing, regular (and/or random) observations, or check-ins, to be made of the subject by the observer. These ongoing observations may be performed by the observer and recorded in an observation log. As described here, the timing of these check-ins may be periodic and/or regular (e.g., every x minutes, where x is 2, 3, 4, 5, 6, 7, 8, 9, 10, 11, 12, 13, 14, 15, etc.). In some variations the check-ins may be continuously performed or substantially continuously (e.g., at <1 min frequency). In some of the variations described herein the check-ins may be random (e.g., selected to be requested at sometime within a defined time interval (e.g., between 2 minutes and 20 minutes, between 2 minutes and 18 minutes, between 2 minutes and 17 minutes, between 2 minutes and 16 minutes, between 2 minutes and 15 minutes, between 2 minutes and 10 minutes, etc.). For example, the observer may be tasked to observe the subject and record the result of the observation in a log. The observation may be selected from a drop-down menu and/or manually entered.

Thus, described herein are methods of using an automated or semi-automated system to assist an observer in monitoring one (or in some cases, more than one) subject to ensure real-time compliance. In any of the methods described herein, the observer may wear, or in some variations hold, an observer device that is executing control logic (e.g., software, firmware, hardware, etc.) that prompts the observer to make the observation(s), may record the observation, indicate if the observer is further from the subject that at a predetermined range (e.g., 3 feet, 4 feet, 5 feet, 6 feet, 7 feet, 8 feet, 9 feet, 10 feet, 12 feet, 15 feet, 20 feet, 25 feet, etc.). The observer device may be wireless device, such as a smartphone, pad (e.g., IPAD), tablet, smartwatch, or any other wearable device that includes a processor for executing the control logic (which may be referred to herein as the observer control logic). The observer device may be configured to be worn by the observer; for example, the observer device may include straps or connectors for connecting to an observer's body (wrist, arm, ankle, leg, torso, etc.) or may be configured to be worn in a holder that attaches to the observer. In some variations the observer device may include an attachment for attaching to an observer's clothing. The observer device may include or may be used with a holder or holster that includes straps or other connectors for connecting the device to the observer, so that the observer device may be worn by the observer.

In general, either or both the observer device and the subject-worn beacon may include an internal motion detector, such as an accelerometer, gyroscope, or the like, that may be used to detect motion of the observer device and/or the subject-worn beacon. This motion may be used by the observer control logic to determine if the observer is sleeping or active, and/or if the observer device is being held or worn, or if it has been set down. The observer device may also include one or more receivers for receiving a wireless signal from a subject-worn beacon. For example, the observer device may include an RF antenna for receiving an RF signal from the subject-worn beacon. The RF antenna may be, for example, a Bluetooth antenna and/or accompanying circuitry for receiving a Bluetooth signal from the beacon. Wireless may refer to any type of radio frequency (RF) (including RF that includes time of flight technology, such as ultrawideband), ultrasonic, or infrared (IR). In variations in which the observe device includes a smartphone, tablet or other similar device that is running observer logic (e.g., software, firmware, etc.), the observe logic may access sensors, such as accelerometers, etc. on the device.

The observer device and/or the observer logic may also include one or more user interfaces for interacting with the observer, including entering observation information. In some variations the observer logic may be configured to monitor the observer (e.g., confirm that the observer is awake, and/or that the observer device is being moved in a manner consistent with being worn by an awake observer), and/or that the observer is within the predetermined range from the selected subject (e.g., patient). The observer logic may also be configured to trigger an alert when the observer is outside of the predetermined range, e.g., immediately or following a delay after leaving the predetermined range, such as a delay of 1 minute, 2 minutes, 3 minutes, 5 minutes, 6 minutes, etc. The observer logic may also trigger (e.g., an alert, alarm, etc.) to indicate after the check-in period that the observer must enter a check-in indicator. The observer logic may also transmit one or more reports to a manager or supervisor agent (including a supervisor or a supervisor agent, such as a remote server) indicating which alarm(s) have been triggered, and any associated information about the observer and/or subject. Manager/supervisor reports may be triggered when the observer fails to respond to one or more alerts or notifications within a response period (e.g., 1 minute, 2 minutes, 3 minutes, 5 minutes, 7 minutes, 8 minutes, 10 minutes, 12 minutes, 15 minutes, etc.). In some variations the alarm(s) may continue to issue on the observer device, concurrently with transmitting the supervisor report.

The observer control logic may be downloaded on to control device (e.g., smartphone, wearable device, etc.), as software, e.g., as an application software ("app"), program, or the like. The observer control logic may include one or more user interfaces, as described in greater detail herein. The observer control logic may communicate (e.g., wirelessly or via a wired connection) with a remote processor (including, but not limited to a remote server) that may analyze, store, and/or transmit the information from the observation device and/or subject-worn beacon. In some variations the control logic is executed on the observer device and may locally process the signal(s) from the subject-worn device, including determining and monitoring the proximity to the subject, and/or determining if the observe device is being held by the observer and/or if the observer is awake or asleep.

In general, the system may include a tamper-resistant beacon that is to be worn by the subject. The tamper-resistant beacon typically emits a signal (or signals) that may be received by the observer device. This signal may be used, e.g., by the observer control logic, to determine the distance between the observer and the subject. In some variations the signal may comprise periodic signals that are repeated with a repetition (e.g., localization repetition) frequency (e.g., 0.01 Hz or greater, 0.015 Hz or greater, 0.02 Hz or greater, 0.05 Hz or greater, 0.1 Hz or greater, 1 Hz or greater, 5 Hz or greater, than 10 Hz or greater, than 20 Hz or greater, greater than 25 Hz, greater than 100 Hz, etc.).

The RF-based subject-worn beacon is typically a wristband (or ankle band) or similar that connects to the subject using a locking fastener that cannot be removed by the subject. See, e.g., U.S. application Ser. No. 15/055,557 (publication no. U.S. 20160253470), herein incorporated by reference in its entirety.

For example, described herein are methods of close-proximity monitoring of a subject, the method comprising: transmitting a signal from a subject-worn beacon that is secured to a subject so that subject-worn beacon cannot be removed by the subject; receiving the signal by an observer device worn by an observer; determining a proximity between the subject and the observer from the signal; prompting the observer to record a subject observation at an interval of 15 minutes or less; and emitting one or more alerts from the observer device when one or more of: the observer is further than a predetermined range from the subject; and the observer does not record a subject observation within a predetermined observation time.

A method of close-proximity monitoring of a subject may include: transmitting a signal from a subject-worn beacon that is secured to a subject so that it cannot be removed by the subject; receiving the signal by an observer device worn by an observer; determining a proximity between the subject and the observer from the signal; prompting the observer, at an interval of 15 minutes or less, to record a subject observation in the observer device; monitoring movement of the observer device; and emitting one or more alerts from the observer device when one or more of: the observer is further than some distance (e.g., 3 feet, 4 feet, 5 feet, 6 feet, 7 feet, 8 feet, 9 feet, 10 feet, 11 feet, 12 feet, 15 feet, 20 feet, 25 feet, 30 feet, etc.) from the subject for greater than a predetermined time interval; the observer device is moved less than a threshold level; and the observer does not record a subject observation within a predetermined observation time.

A method of close-proximity monitoring of a subject may include: transmitting a signal from a subject-worn beacon that is secured to a subject so that it cannot be removed by the subject; receiving the signal by an observer device worn by an observer; determining a proximity between the subject and the observer from the signal; prompting the observer, at an interval of 15 minutes or less, to record a subject observation in the observer device; confirming that the observer is awake (and/or not moving enough to exceed a movement threshold); emitting one or more alerts from the observer device when one or more of: the observer is further than a predetermined range from the subject for greater than a predetermined time interval; the observer not awake; and the observer does not record a subject observation within a predetermined observation time; and transmitting a report to a supervisor if the observer does not comply with the one or more alerts within a compliance time period.

In any of these methods, prompting the observer may include prompting the observer at a random time interval of, e.g., between 1 minute and 20 minutes (e.g., between 1 min and 18 min, between 1 min and 15 min, between 3 min and 20 min, between 3 min and 18 min, between 3 min and 15 min, between 5 min and 20 min, between 5 min and 18 min, between 5 min and 15 min, etc.). For example, prompting the observer may comprise prompting the observer at an interval of 10 minutes or less. The observer may be prompted on the observation device (e.g., by the observation control logic running on the observation device) and the prompt may be visual, audible and/or tactile. For example, the prompt may be a user interface screen displayed on a display of the observer device that requests an observation be entered. The observation may be entered into the observation device (e.g., from a drop-down menu, multiple choice selection, and/or keyed in). In some variations, the observation may be manually recorded, e.g., in a notebook, clipboard, etc.

As mentioned, any of these methods may include confirming that the observer is awake or determining a likelihood that the observer is awake or asleep. The methods and apparatuses described herein may also determine if the subject is awake or asleep. For example, the observation device may include one or more motion sensors (e.g., accelerometers, etc.) and the observation control logic may locally determine (or alternatively may transmit to a remote processor to determine) if the sensed motion is above a threshold that indicates that the observation device is being worn by an awake observer. In variations in which the observation device determines (or receives a determination) that the observation device is moved below a minimum threshold per unit time (e.g., indicating that the observer is not active and/or awake), the observation device may emit one or more alert, e.g., to rouse the observer. The observation control logic may continuously monitor to determine that the minimum movement (e.g., awake/asleep status) is achieved, or it may determine this only at or immediately before prompting an observation. For example, emitting one or more alerts from the observer device when the observer is further than a predetermined range from the subject may include emitting one or more alerts when the subject is further than the predetermined range for greater than a predetermined time interval.

The observation device may emit an alert or more than one type of alerts. The alerts may be one or more of: an audible alert, a tactile alert, and a visual alert. In some variations, the alerts may be made inaudible, so that they will not disturb the subject (e.g., who may be sleeping). Different alerts (e.g., different patterns of vibration, tone, intensity, etc.) may be used to indicate alerts corresponding to different situations, such as exceeding the monitoring distance, prompting for an observation, etc.). The intensity of the alert may be scaled to the duration that the alerting condition has persisted.

As mentioned above, any of these methods and apparatuses may be configured to issue one or more reports in addition or instead of emitting an alert. For example, in some variations the apparatus may transmit a supervisor report to a supervisor (e.g., a server, computer, etc., remote processor) that describes the alert. This report may be referred to herein as a supervisory alert. The supervisory report/alert may be transmitted if the observer does not address the one or more alerts within a compliance time period (e.g., within about 1 minute, within about 2 minutes, within about 3 minutes, within about 4 minutes, within about 5 minutes, within about 7 minutes, within about 10 minutes, within about 12 minutes, within about 15 minutes, within about 20 minutes, etc.), for example of about 1 minute (e.g., 2, 3, 4, 5, 7, 10, 15, etc. min) or more. Alternatively, in some variations the supervisory report/alert may be transmitted concurrently with the alert.

In general, the methods and apparatuses described herein may be configured to operate with or without a wireless network (an in such a manner that the user/observer does not necessarily realize that the network connection is not present). For example, the observer device may cache observations and collected data for later transmission to a remote database. Thus, observer device may be configured to periodically (every x minutes, every x hours, etc.) transmit data to the remote database, but this periodic transmission may occur only when the device detects it has a network connection As mentioned above, the signal from the subject-worn beacon may be transmitted continuously or periodically. For example, the signal from the subject-worn beacon may be transmitted from the subject-worn beacon with a periodic frequency 0.01 Hz or greater. In some variations the beacon may transmit continuously; the magnitude (or absence) of the transmission may be used as a trigger.

Also described herein are apparatuses, including systems, for close-proximity monitoring. These apparatuses may be configured to perform any of the methods described herein. For example, a system for close-proximity monitoring subjects may include: a subject-worn beacon, wherein the subject-worn beacon is configured to wirelessly transmit a signal and further wherein the subject-worn beacon comprises a tamper-resistant attachment to the subject (e.g., via a tamper resistant latch or other mechanism) that is configured to secured to the subject-worn beacon to the subject so that the subject-worn beacon cannot be removed by the subject; a memory comprising computer-program instructions, that, when executed by one or more processors of a wearable observer device, perform a computer-implemented method comprising: receiving the signal in the wearable observer device; determining a proximity between the subject and the observer from the signal; prompting the observer to record a subject observation at an interval of 15 minutes or less; and emitting one or more alerts from the observer device when one or more of: the observer is further than a predetermined range from the subject; and the observer does not record a subject observation within a predetermined observation time.

For example, a system for close-proximity monitoring subjects may include: a subject-worn beacon, wherein the subject-worn beacon is configured to wirelessly transmit a signal and further wherein the subject-worn beacon comprises a tamper-resistant connection (e.g., latch) that is configured to be secured to the subject-worn beacon to the subject so that the subject-worn beacon cannot be removed by the subject; a memory comprising computer-program instructions, that, when executed by one or more processors of a wearable observer device, perform a computer-implemented method comprising: determining a proximity between the subject and the observer from the signal; prompting the observer, at an interval of 15 minutes or less, to record a subject observation in the observer device; monitoring movement of the observer device; and emitting one or more alerts from the observer device when one or more of: the observer is further than 10 feet from the subject for greater than a predetermined time interval; the observer device is moved less than a threshold level; and the observer does not record a subject observation within a predetermined observation time; and transmitting a report to a supervisor if the observer does not comply with the one or more alerts within a compliance time period.

In any of these systems, the computer-implemented method step of prompting the observer may comprise prompting the observer at a random time interval of between 1 minute and 15 minutes. For example, the computer-implemented method step of prompting the observer may comprise prompting the observer at an interval of 10 minutes or less.

In some variations, the computer-implemented method further comprises confirming that the observer is awake and wherein emitting one or more alerts from the observer device further comprising emitting the one or more alerts when the observer is not awake. For example, the computer-implemented method may further comprise confirming that the observer is awake based on an activity level measured from the observer device and wherein emitting one or more alerts from the observer device further comprising emitting the one or more alerts when the observer is not awake.

As mentioned above, the predetermined range may be, e.g., 3, 4, 5, 6, 7, 8, 9, 10, 11, 12, 15, 20, or 25 feet or more (e.g., 10 feet or greater).

The computer-implemented method step of emitting one or more alerts from the observer device may include emitting one or more alerts from the observer device when one or more of: the observer is further than a predetermined range from the subject for greater than a predetermined time interval. For example, the computer-implemented method may further comprise transmitting a report to a supervisor if the observer does not comply with the one or more alerts within a compliance time period. The compliance time period may be 1 minutes or more (e.g., 2, 3, 4, 5, 6, 7, 8, 9, 10, 15, 20, etc. minutes or more). In general, a report may be transmitted by text message, email, or any other notification type.

The computer-implemented method step of emitting one or more alerts from the observer device may comprise emitting one or more of: an audible alert, a tactile alert, and a visual alert.

In any of these systems, the signal may be transmitted from the subject-worn beacon with a periodic frequency 0.01 Hz or greater; in some variations, the signal is continuously transmitted from the subject-worn beacon.

Also described herein are methods of close-proximity monitoring that are configured so that that the subject is continuously monitored even when transferring between observers; this may be guaranteed by the configuration of the system, which may require that a second observer is logged in to observe the same subject before the first observer can log out. For example, a method of close-proximity monitoring of a subject may include: logging in a first observer for line-of-sight monitoring of a subject; logging in a second observer for line-of-sight monitoring of the subject; and logging the first observer out of line-of-sign monitoring only after the second observer has been logged in.

In some variations, a method of close-proximity monitoring of a subject may include: logging in a first observer for line-of-sight monitoring of a subject, wherein the line-of site monitoring includes: receiving a signal from a subject-worn beacon; determining a proximity between the subject and the first observer from the signal; prompting the first observer to record a subject observation at an interval of 15 minutes or less; and emitting one or more alerts when one or more of: the observer is further than a predetermined range from the subject; and the observer does not record a subject observation within a predetermined observation time; logging in a second observer for line-of-sight monitoring of the subject; and logging the first observer out of line-of-sign monitoring only after the second observer has been logged in.

In any of these methods and apparatuses, logging in the first observer may comprise logging in the first observer into an automated monitoring system. In some variations, logging in the first observer comprises selecting the subject from a list of subjects.

In general, receiving the signal from the subject-worn beacon may comprise receiving the signal from a subject-worn beacon that is secured to a subject so that it cannot be removed by the subject. Prompting the observer may comprise prompting the observer at a random time interval (e.g., between 1 min and 20 min, between 1 minute and 15 minutes, between 3 min and 20 min, between 3 min and 15 min, etc.). For example, prompting the observer may comprise prompting the observer at an interval of 10 minutes or less.

Any of these methods and apparatuses may include confirming that the observer is awake and wherein emitting one or more alerts from the observer device further comprising emitting the one or more alerts when the observer is not awake. For example, any of these methods and apparatuses may include confirming that the observer is awake based on an activity level measured from the observer device and wherein emitting one or more alerts from the observer device further comprising emitting the one or more alerts when the observer is not awake.

As mentioned above, emitting one or more alerts from the observer device may comprise emitting one or more alerts from the observer device when the observer is further than a predetermined range from the subject for greater than a predetermined time interval (e.g., 1 min, 2 min, 3 min, 4 min, 5 min, 6 min, 7 min, 8 min, 9 min, 10 min, 15 min, 20 min, etc.).

Also described herein are methods of detecting unwanted or prohibited contact between subject's wearing subject-worn beacons. In some cases, multiple subjects may be co-housed, including in the same room or nearby rooms. It may be desirable to detect (in order to prevent or limit) inappropriate or likely inappropriate interactions between patients, such as fighting or sexual congress. In some variations the subject-worn beacons may sense proximity relative to each other and may transmit this information to an observer device or other sensing/monitoring device (including static, such as wall-mounted observer devices, relays or links to remote monitoring and/or remote observer devices). This may be detected using RF energy (e.g., Bluetooth, etc.) or other means, from which distance may be triangulated or otherwise determined directly. However, in some variations it may be desirable, e.g., to extend or protect battery charge and/or life, to use subject-worn beacons that do not receive signals and/or that only transmit.

Thus, described herein are methods of detecting contact between subjects (e.g., unwanted or prohibited contact, including assault). For example, described herein are methods (and systems for performing these methods) that include: receiving a signal from a first subject-worn beacon that is secured to a first subject (e.g., in a tamper-resistant manner), wherein the signal from the first subject-worn beacon comprises a unique identifier specific to the first subject-worn beacon and movement data associated with the first subject-worn beacon; receiving a signal from a second subject-worn beacon that is secured to the second subject (e.g., in a tamper-resistant manner), wherein the signal from the second subject-worn beacon comprises a unique identifier specific to the second subject-worn beacon and movement data associated with the second subject-worn beacon; comparing the movement data associated with the first subject-worn beacon with the movement data associated with the second subject-worn beacon; and triggering an alert if the movement data associated with the first subject-worn beacon and the movement data associated with the second subject-worn beacon are coordinated in time.

For example, a method may include: receiving, a monitor or observer device, a signal from a first subject-worn beacon that is secured to a first subject in a tamper-resistant manner that prevents the first subject-worn beacon from being removed by the first subject, wherein the signal from the first subject-worn beacon comprises a unique identifier specific to the first subject-worn beacon and movement data associated with the first subject-worn beacon; receiving, the monitor or observer device, a signal from a second subject-worn beacon that is secured to a second subject in a tamper-resistant manner that prevents the second subject-worn beacon from being removed by the second subject, wherein the signal from the second subject-worn beacon comprises a unique identifier specific to the second subject-worn beacon and movement data associated with the second subject-worn beacon; comparing the movement data associated with the first subject-worn beacon with the movement data associated with the second subject-worn beacon; and triggering an alert if the movement data associated with the first subject-worn beacon and the movement data associated with the second subject-worn beacon are coordinated in time.

The signals may be received by a monitor or observer device that is remote to the first and second patient. The signals from the first and second subject-worn beacons may be received continuously or periodically (e.g., within every x seconds, every x minutes, etc. where x is 1, 2, 3, 4, 5, 6, 7, 8, 9, 10, etc.) on a regular or irregular schedule). The signals from the first and second subject-worn beacons including time data.

Comparing the movement data may include comparing the frequency and intensity of movement data to determine correlation between the movement data of the first and second subject-worn beacons, and triggering the alert where the correlation is above a threshold for correlation, indicating that the movement data is coordinated in time.

The alert may be triggered if the movement data is coordinated and it is collected during a predefined sleeping period. In some variations, triggering the alert comprises notifying a minder. The alert may include an alarm, a message, or the like.

The movement data associated with the first subject-worn beacon and the movement data associated with the second subject-worn beacon may be coordinated in time where the intensities of both the movement data associated with the first subject-worn beacon and the movement data associated with the second subject-worn beacon are above a movement intensity threshold and overlap in time.

Any of these methods and apparatuses may include transmitting a report to a supervisor if the observer does not comply with the one or more alerts within a compliance time period (e.g., 1 minutes or more, 2 min or more, etc.). Other examples of systems for monitoring a subject are described, for example, in U.S. patent application Ser. No. 16/344,506, titled "TAMPER RESISTANT ONE-TIME USE WRISTBAND AND CLASP and ALGORITHM TO ENHANCE THE PRACTICAL USE OF RADIO FREQUENCY FOR PROXIMITY BETWEEN TWO OR MORE ENTITIES," filed on Sep. 14, 2017, herein incorporated by reference in its entirety.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

In general, described herein are close-proximity monitoring apparatuses and methods of close-proximity monitoring.

Figure 1A:
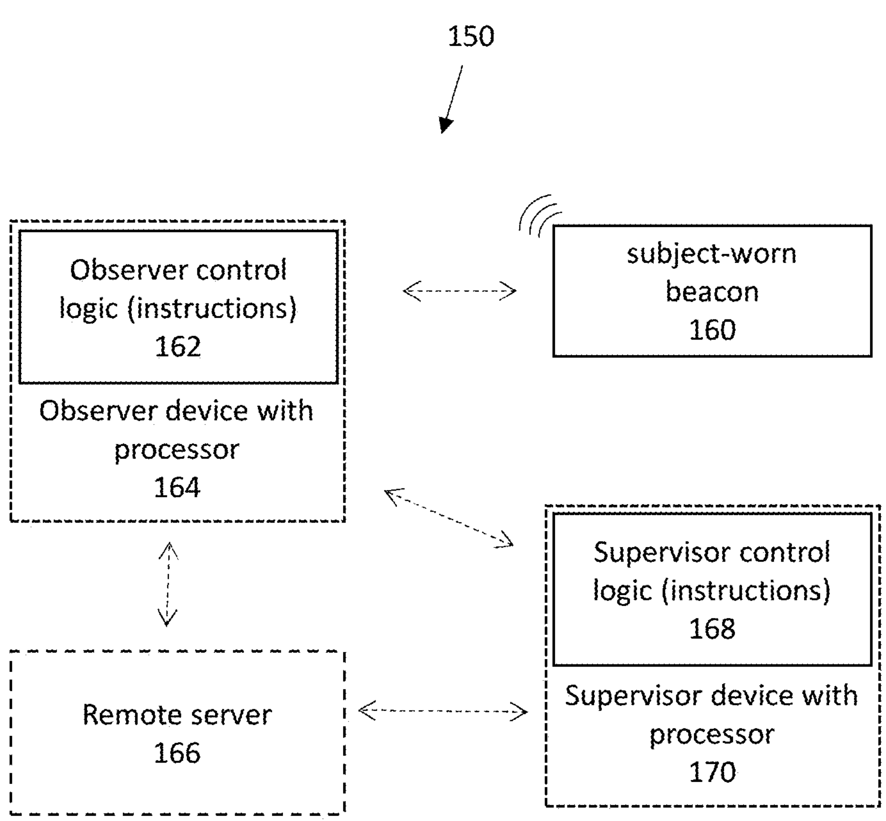
FIG. 1A schematically illustrates one example of a system for close-proximity monitoring a subject as described herein.

For example, FIG. 1A shows one example of an apparatus for close-proximity monitoring of a subject. A system 150 for close-proximity monitoring of a subject may include a subject-worn beacon 160 that is configured to wirelessly transmit a signal or signals. The apparatus may also include executable control logic 162 (e.g., code) that may be executed by a control device such as a smartphone or other wearable device, e.g., in the processor of such as device 164. The wearable control device may be optionally provided, or it may use an existing device, e.g. provided by the observer or another. In general, the observer device may be configured to be worn on the observer's body (e.g., arm, etc.) and may wireless connect with one or more remote servers (e.g., cloud server) 166, and may directly or indirectly connect to a supervisor device including a processor 170 onto which supervisor control logic 168 has been loaded. The supervisor control logic may include instructions for receiving, storing, analyzing and/or retransmitting data from the observer and/or observer device; this data may include observations (e.g., time-stamped observations) from the observer and/or information about one or more alerts, such as supervisor reports.

In operation, the signal transmitted by the beacon may be identified or associated with the particular device worn by the subject and/or the subject directly, for example, when the subject-worn device is registered to the subject. For example, the signal may be a code that is uniquely associated with the subject-worn beacon. In some variations the signal encodes information about the status of the subject wearing the beacon. For example, the signal may encode identifying information about the subject (e.g., name, age, patent number, chart number, etc.). In some variations the signal may encode information on the status of the subject (heart rate, skin temperature, etc.). For example, the information may be encoded in the transmitted signal in a predefined manner so that when the signal(s) is/are received by an observer device, the signal may be used to identify the beacon and/or the subject associated with the beacon.

The observer device may locally process the signal(s) received from the beacon and/or it may retransmit the signal information to a remote processor and/or a supervisor device for further processing. The observer device, executing observer control logic, may therefore determine or receive information about the actual proximity to the subject-worn beacon based on the signal(s) received from the beacon. One or more techniques may be used to determine the proximity between the observer device and the beacon on the subject. For example, the signal strength and/or intensity may be used. In some variations time-of-flight information may be used.

In some variations, the beacon may directly or indirectly communicate with either the observer device (e.g., indirectly via a relay or other transmitting/receiving (Tx/Rx) unit within the subject's room), and/or directly or indirectly with a supervisor device. Similarly, the observer device may directly or indirectly communicate with the supervisor device. For example, the system may be configured for direct transmission (Tx/Rx) between the observer and the supervisor device (which may also be referred to as a staff device) rather than passing through the remote server. Various exemplary configurations are shown by the dashed lines in FIG. 1.

Figure 1B:
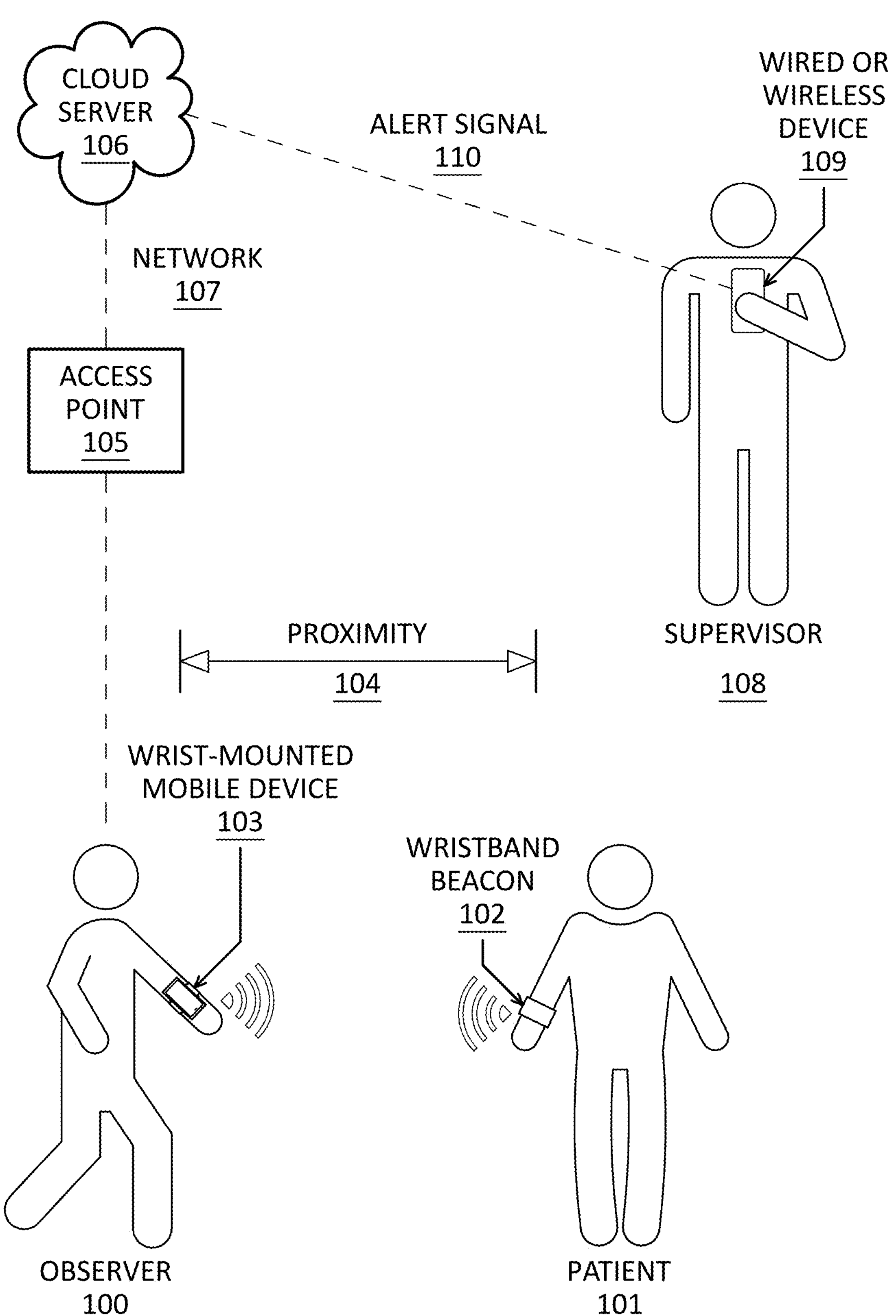
FIG. 1B schematically illustrates a method of using a system for close-proximity monitoring a subject as described herein.

FIG. 1B illustrates an example of the operation of a system 151 for close-proximity monitoring of a subject. In FIG. 1B, the system is configured as a wireless subject monitoring system 151 that may allow an observer 100 to more accurately and effectively monitor one or more subjects 101 in close proximity or at least line-of-sight. The subject 101 wears a wrist or leg mounted wireless transmitter or beacon 102 that is capable of broadcasting an RF signal 111. The subject-worn beacon will typically be attached to the subject using a tamper-resistant band or fastening mechanism. This fastening mechanism, and therefore the beacon, may therefore be configured to prevent the subject (e.g., patient) from removing the beacon. The observer in this example wears a mobile device 103, e.g., an observer device, shown on the wrist, that has hardware and software capable of detecting the RF signal from the subject's beacon. The observer device (e.g., phone, iPod, etc.) may continuously read the subjects' beacon RF advertisement 111 and may monitor the proximity, power level and/or direction of the signal. As mentioned above, in some variations the observer device may be a wearable device having a processor that may be controlled by an executable observer control logic (e.g., software, firmware, etc., such as an application software or "app"). The observer control logic may continuously compare the received subject advertisement signal to a threshold setting in the device software to determine if the observer is still in range of the subject wearing the beacon. As mentioned, in some variations additional subject information, such as subject body temperature, movement, and/or heart rate, etc. may be included and encoded in the signal(s) broadcast by the beacon.

The observer control logic may also use one or more sensors on the control device (such as an accelerometer, gyroscope, etc., to detect motion and temperature sensors to detect the temperature of the observer; any biometric may be used), and this information may be locally, e.g., on the control device, or remotely used to confirm that the user is holding, wearing, or otherwise connected to the observer device, rather than setting it down, or perhaps falling asleep. For example, an accelerometer/gyro reading of the observer's device may be compared to a threshold setting in the device software to determine if the observer has taken the device off or fallen asleep as indicated by minimal to no motion activity. In general a sensor that detect a biometric for the observer may be used to determine that the observer is still holding/connected to the device (and has not set it down/taken it off) and/or may be used to determine an activity level for the observer.

In some variations the observer wearable device may include one or more temperature sensors instead or in addition to motion detection. Temperature sensing may be used to detect, for example, when or if an observer has removed the device (e.g., is no longer wearing the device). For example, in some variations the sensors (e.g., temperature sensor) is part of the observer device (such as a smartwatch, etc.) that may be worn in intimate contact with the observers skin and detect body temperature or the lack of. In some variations the temperature sensor may be part of a holder or wearable attachment that may be worn with (or as part of) a wearable device.

In any of the apparatuses and methods described herein, the system may separately monitor proximity (including contact) between the observer and the patient, not limited to indicated observation times. In some variations the apparatus may continuously monitor or detect contact between the observer and the patient. This proximity detection may be monitored continuously or discretely (e.g., every 0.5 second or less, every 1 second or less, every 2 seconds or less, every 3 seconds or less, every 5 seconds or less, every 10 seconds or less, every 20 seconds or less, every 30 seconds or less, every 1 min or less, every 2 min or less, etc.). In some variations proximity detection may be concurrent with the observation interval, or a proximity detection may be made at the time of an observation in addition to ongoing continuous or periodic monitoring.

The observer device (via the control of the observer control logic) may also or alternatively present the observer with requests to perform observations. These observation reminders can be set at a fixed interval or a randomized time. These observation requests may help to keep the observer focused and engaged with the subject. If any of the alert conditions as described above are reached, the observer control logic may initiate a progressive set of steps to have the observer correct the deficiencies and/or may alert the supervisor(s) that the observer is no longer in proximity of the subject, has fallen asleep or is otherwise inattentive. Alerts can be initiated at the observer device and/or sent to the remote server to be sent out to predetermined recipients, including the supervisor. Leading up to supervisory alerts, the control logic can send audible, visual and/or vibratory stimulation to the observer through their wearable (e.g., wrist-mounted) observer device as reminders to correct deficiencies. The observer device software (e.g., the observer device) may have observer control logic designed to enable frequent changes in observers without breaks in the prescribed one-to-one constant monitoring.

Any of the apparatuses and methods described herein may use the beacon advertisement RF power level (e.g., received signal strength indicator, or RSSI) to ensure proximity is being maintained.

An observer's device that is tightly coupled to the observer's wrist may help ensure activity levels can be measured without false alarms. Thus, any of these apparatuses and methods described herein may be used with an observer device that is worn on the observer, or may be held by the observer. In some variations, the observer device may be coupled to the observer using a tamper-resistant connector (e.g., strap, etc.) for securing the observer device to the observer's wrist or may include a mechanism that indicates when the wrist mounting is removed, such as an open circuit indicator. Thus, the observer device or an associated device may include a compliance sensor or indicator that indicates (or may be analyzed, e.g., by the observer control logic and/or the supervisor control logic) to determine when the observer is in compliance with the operation of the device and is not sleeping or has not removed the observer device. Because, in some variations, loose-fitting observer devices may not measure low activity levels leading to false alarms that the observer was sleeping or had taken the device off). The observer device may include a holder or mount that may be configured to secure the observer device (phone, pad, etc.), to an arm, wrist or hand of the user.

As mentioned, the observer device may be configured to provide a visual, audible and/or tactile (vibration) feedback to the observer through the observer device to prompt them to correct their activity level with the observer device prior to escalating to a supervisory alert thereby preventing alarm fatigue.

In any of the apparatuses and methods described herein, the apparatus may be configured to permit allowable deviations for activity level, proximity and observation response time, e.g., over some interval (delta) of time before the alert or alarm is triggered and/or before a report is generated or alarms are sent. This may prevent or limit excessive alarms or deviations from threshold conditions that are dangerous and might create alarm fatigue if the alert were allowed to propagate to the supervisor prior to self-correction by the observer. For example, the system may be configured to wait for a response to the request for observation before triggering an alarm. In some variations the system may be configured to wait at least 1 minute, 2 minutes, 3 minutes, 4 minutes, 5 minutes, 6 minutes, 7 minutes, etc. and may re-prompt (e.g., with one or more visual, audible, tactile, etc. prompt) within this time period before triggering an alarm.

In general, any of these apparatuses and method may be configured to request observations from the observer at preset or randomized observation prompts to the observer. For example, the observer may be configured to request an observation every x minutes, where x is 2, 3, 4, 5, 6, 7, 8, 9, 10, 11, 12, 13, 14, 15, etc. These requested observations may be check-ins. The duration between check-ins may be adjusted based on the observed data entered. For example, more frequent observations may be requested when the subject is agitated, and less frequent observations when the subject is sleeping.

As mentioned above, the proximity signal emitted by the subject-worn beacon may be radiofrequency (RF), such as Bluetooth, or may be any other wireless modality, such as ultrasound, infrared, or some combination thereof. For example, if ultrasound is used, proximity sensing may be performed by detecting intensity and/or by time of flight information, in which the timing of the signal emitted by the beacon is known by the observer device and may be used to determine distance. In any of the apparatuses and methods described herein the proximity signal emitted by the subject-worn beacon may be analyzed by the observer (or by a processor in communication with the observer) to determine proximity between the observer device (and presumably the observer wearing/holding the observer device) and the patient. In some variations this proximity is explicitly calculated. In some variations the proximity is not measured as a distance, but it estimated based on, e.g., the signal strength (e.g., the Received Signal Strength Indicator, or RSSI); thus, a direct measure or estimate of signal strength may be used without requiring conversion to actual distance units.

In some variations rather than, or in addition to, direct communication between the beacon and the observer device to determine proximity between the two, one or more additional room beacons or gateways may be used. For example, a room beacon or gateway may be established near the subject and may track the relative positon of the beacon worn by the subject relative to the room beacon or gateway, and/or the relative position of the observer to the room gateway or beacon. The proximity of the user-worn beacon to the observer device may then be triangulated.

Figure 2:
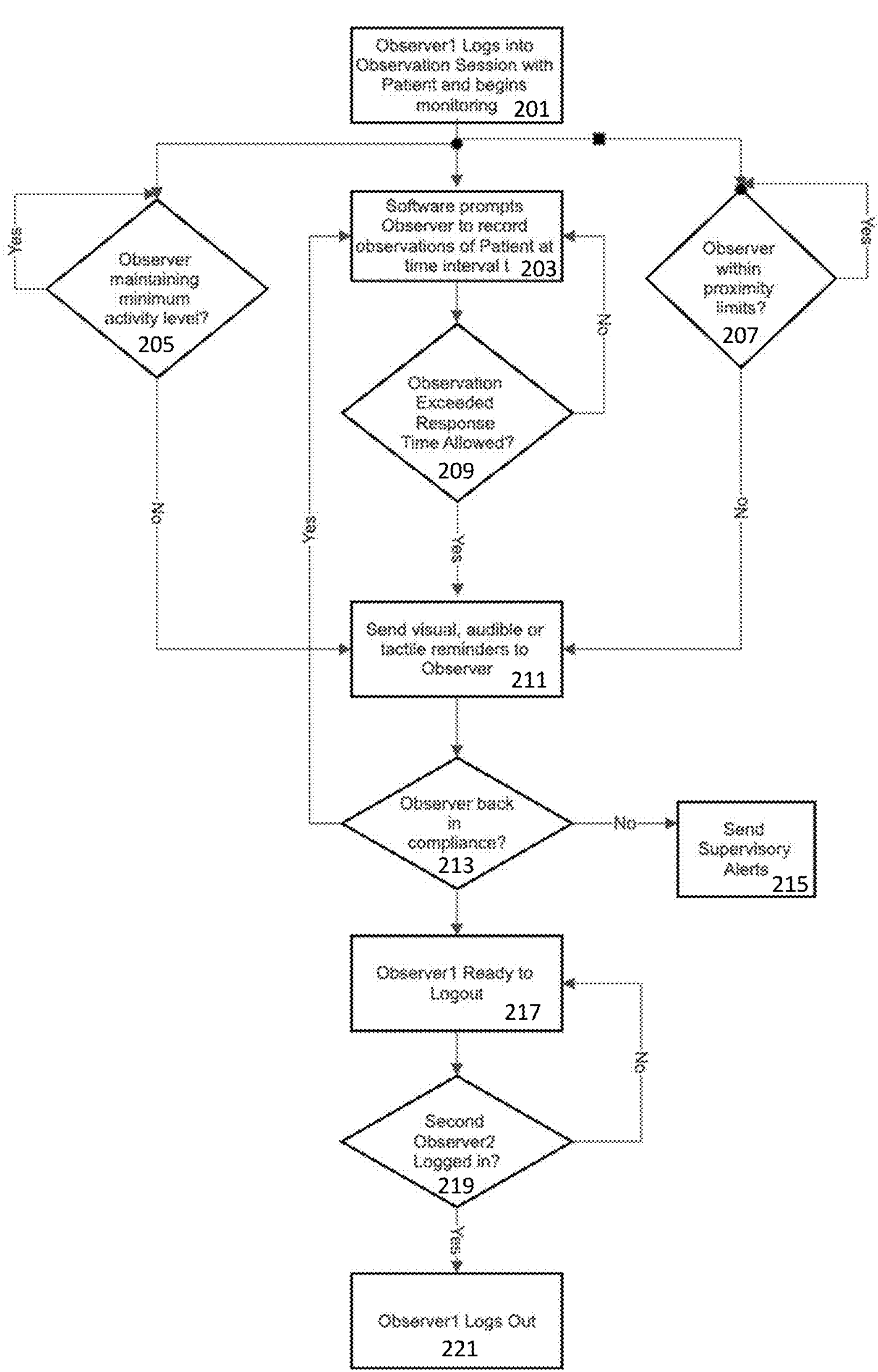
FIG. 2 is a process flow diagram illustrating one example of a method of close-proximity monitoring a subject as described herein.

FIG. 2 illustrates one example of a process flow for one method of close-proximity monitoring of a subject. In this example, the observer first logs into an observation session by selecting the subject to be monitored and begins monitoring 201. During the observation, the observer control logic (software) running on the observer device that may be worn or held by the observer prompts the observer to record observations of the subject (patient) at continuing time intervals, t, 203. As mentioned, these time intervals may be set, adjusted by the observation control logic (e.g., based on the reported observations, time of day, etc.) and/or random within a defined range. The software may continue to prompt the observer to enter the observation within a response wait time period. If the observer does not respond within this response wait time 209, the observer control logic may trigger an alarm, reminding the observer 211. The reminder may be visual, audible, and/or tactile. The alarm may continue for an alarm time period (e.g., 10 seconds, 20 seconds, 30 seconds, 45 seconds, 1 minute, 2 minutes, 3 minutes, 4 minutes, 5 minutes, etc.) to allow the observer to respond and remedy the alarm by entering the observation or by indicating that no observation was done (a reason may be provided or not) 213. If the alarm is not remedied within a report time period (which may, in some instances be set to 0 seconds), which may be the same as, shorter than or longer than the alarm time period, the control logic may trigger a supervisor report/alert 215, reporting the failure to make the observation.

In some variations, the observer control logic may in parallel monitor the proximity of the observer relative to the subject (e.g., patient) 207. As described above, the proximity may be detected from the signal emitted by the beacon. The method or apparatus may be configured to determine proximity continuously (e.g., each time the signal is received from the beacon) and/or at discrete times, such as immediately before prompting to record an observation of the subject, which may reduce battery usage, or at some other time interval (e.g., every s seconds, where s is 0.01, 0.05, 0.1, 0.5, 1, 2, 3, 4, 5, 10, 15, 20, 30, 40, 50, 60, 120, etc.). If the observer is not within the proximity limits set by the observer control logic, the observer control logic may trigger an alarm, reminding the observer to return within proximity of the subject 211. The reminder may be visual, audible, and/or tactile. The alarm may continue for a proximity response time period (e.g., 10 seconds, 20 seconds, 30 seconds, 45 seconds, 1 minute, 2 minutes, 3 minutes, 4 minutes, 5 minutes, etc.) to allow the observer to respond and remedy the alarm. Thus, the observer control logic (software) may prompt the observer to return to the proximity of the subject within a proximity response wait time period. If the observer does not return within proximity within this proximity response wait time (e.g., the alarm is not remedied) within a proximity report time period (which may, in some instances be set to 0 seconds), which may be the same as, shorter than or longer than the proximity response wait time period, the control logic may trigger a supervisor report/alert 215 to report this proximity alarm.

In some variations, the observer control logic may in parallel monitor the movement of the observer device and/or directly monitor the movement (or activity level) of the observer 205. The movement of the observer device may be a proxy for the awake/asleep (e.g., alertness) status of the observer. If the observer device is not moved above a level within defined limits set by the observer control logic, the observer control logic may trigger an alarm, indicating that the observer device should be moved to indicate the alertness of the observer 211. The alert may be visual, audible, and/or tactile. The alert may continue for an alertness response time period (e.g., 10 seconds, 20 seconds, 30 seconds, 45 seconds, 1 minute, 2 minutes, 3 minutes, 4 minutes, 5 minutes, etc.) to allow the observer to respond and remedy the alarm. Thus, the observer control logic (software) may prompt the observer to move their body (if the observer device is worn) or the observer device directly (if held) within the alertness response wait time period. If the observer does not respond within this alertness response wait time (e.g., the alarm is not remedied) within an alertness report time period (which may, in some instances be set to 0 seconds), which may be the same as, shorter than or longer than the alertness response wait time period, the control logic may trigger a supervisor report/alert 215 to report this alertness alarm. The activity level/movement of the observer device may be detected periodically or continuously (e.g., as part of a moving window of movement over time).

The reminders (e.g., alarms and/or alerts) may be different between the observation, proximity and activity reminders, or they may be the same. In some instances, a single alert or alarm may be used, in order to avoid overwhelming the observer, and because the same response may remedy more than one of these (e.g., moving closer to the subject may remedy the activity reminder, making the observation may remedy the activity reminder, etc.).

EXAMPLES

In one variations, the subject (e.g., patient) wears a beacon. A wearable electronics device including a processor (the "observer device," e.g., an iPod™) may be strapped to the observer's wrist. Observer control logic (e.g., software) running on the observer device may monitor accelerometer/gyro readings from the wearable observer device to determine if the observer is awake and wearing the observer device. A lack of movement of the observer device could indicate that the user has put the observer device down and walked away. Alternatively, or additionally, in some variations a tamper-resistant observer device wristband may be worn by the observer while observing the user.

Figure 3:
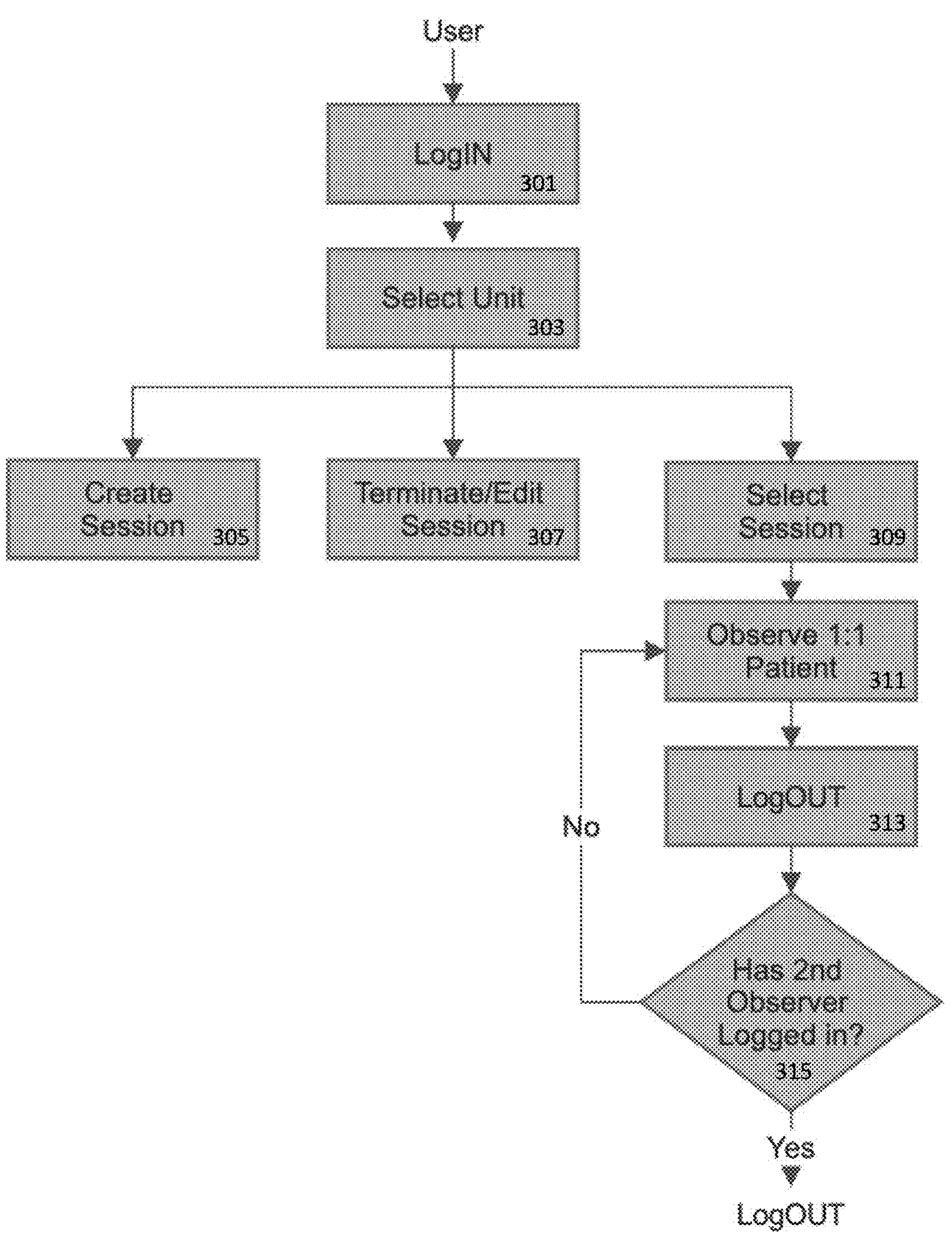
FIG. 3 illustrates one example of a process flow for operating a system for close-proximity monitoring of a subject, as described herein.

FIG. 3 illustrates one example of a process flow for operating a system for close-proximity monitoring of a subject, as described herein. As shown in FIG. 3, the observer (user) may log in to the controlling software (e.g., the supervisor control logic/software), which may be accessed through the observer control logic on the observer device, and may select a beacon unit 303 to monitor. This beacon unit may be the home unit of the subject (patient) designated for 1:1 monitoring.

In some variations, a supervisor may have the ability to Create 305, Terminate 307, or Select 309 an observation Session. Create and Terminate Session may be administrator functions and may be restricted via roles/permissions, e.g., accessed through the supervisor control logic/software. Observers (users) may be assigned to subjects and sessions via an auto-assign feature that may enable any user to login to any 1:1 session. For example, an observer may be assigned to monitor a subject that they are in close proximity to automatically. They may then observer the subject 311, as described above, for their period of observation.

An observer may be able to see and log into a session once it is created. An observer may only be able to log in to one observer device at any one time. An observer may only logout 313 if a second observer has logged into the session simultaneously 315, or if an Administrator has terminated the session. The rationale behind a simultaneous second observer is to ensure that there is always an observer assigned to the 1:1 subject as long as the session exists. The second observer may log into the session via a second observer device or via the first observer device. If a session is terminated by an Administrator, it should simultaneously: automatically log the observer out of the session and transfer the subject out of the 1:1 session and into a home unit session.

An administrator (e.g., supervisor) may be required to create or terminate sessions for a subject. Once a session is terminated, it may end and the session may disappear, meaning it will no longer be shown or be available. In other words, it may be deleted as a standing session. Supervisors/administrators may have permission to create and terminate sessions. In the user interface, observer restrictions may be "greyed out" and not accessible without the appropriate permission. As described above, reports may be generated automatically or manually. Reports may provide an audit trail. An audit trail may include: a time stamp for user login and logout, and/or session creation, termination and observation.

Figure 4A:
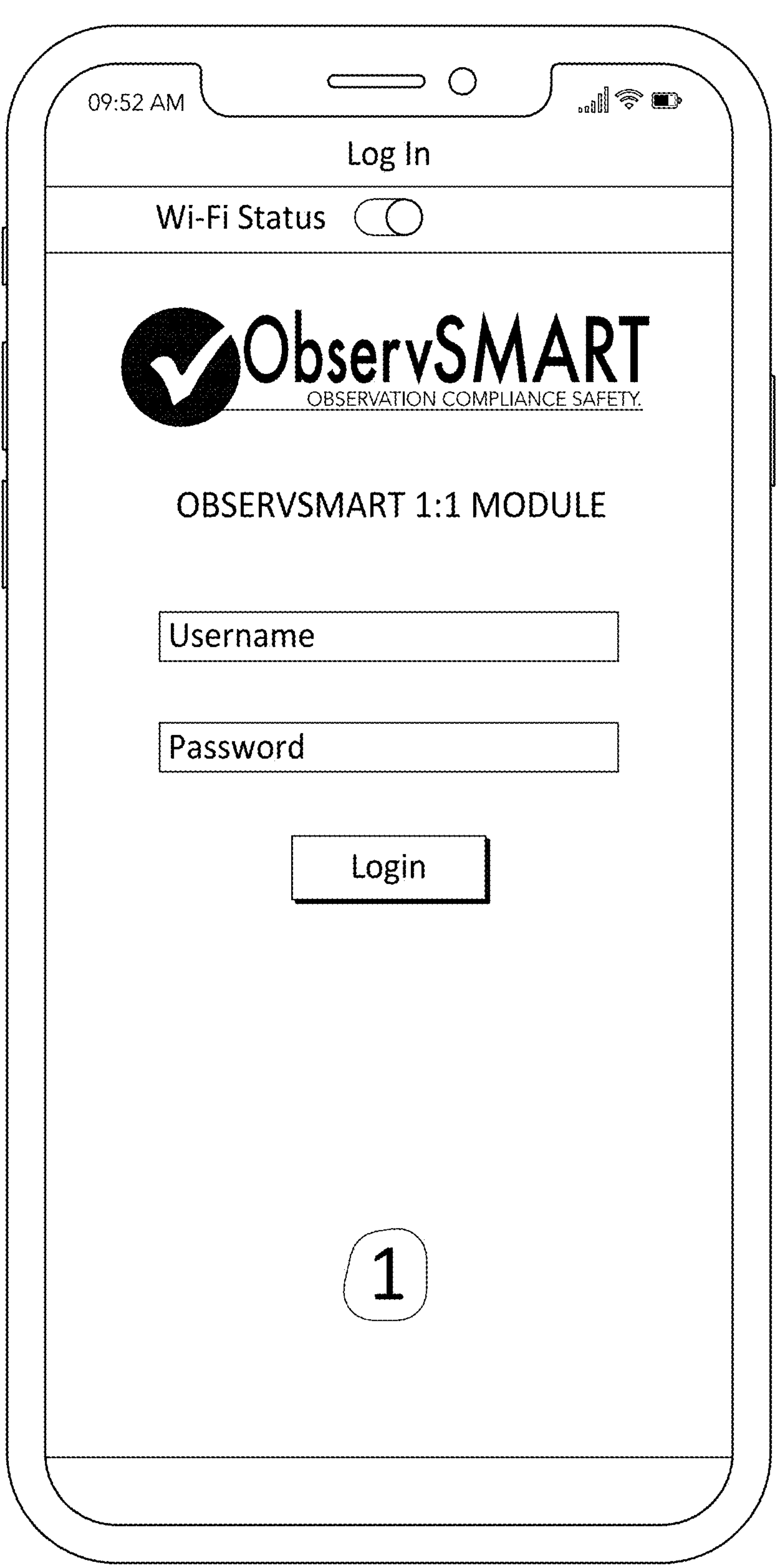
FIGS. 4A-4F show exemplary user interfaces (UI) for a system for close proximity monitoring of a subject, as described herein.

FIGS. 4A-4D illustrate example of a user interfaces for an observer device that may be used. For example, FIG. 4A shows an example of a login interface for a user login. In this example, the user may enter his username and password. This may be proceeded by a facility code entry popup with the same options for re-entry or save.

Figure 4B:
Figure 4C:
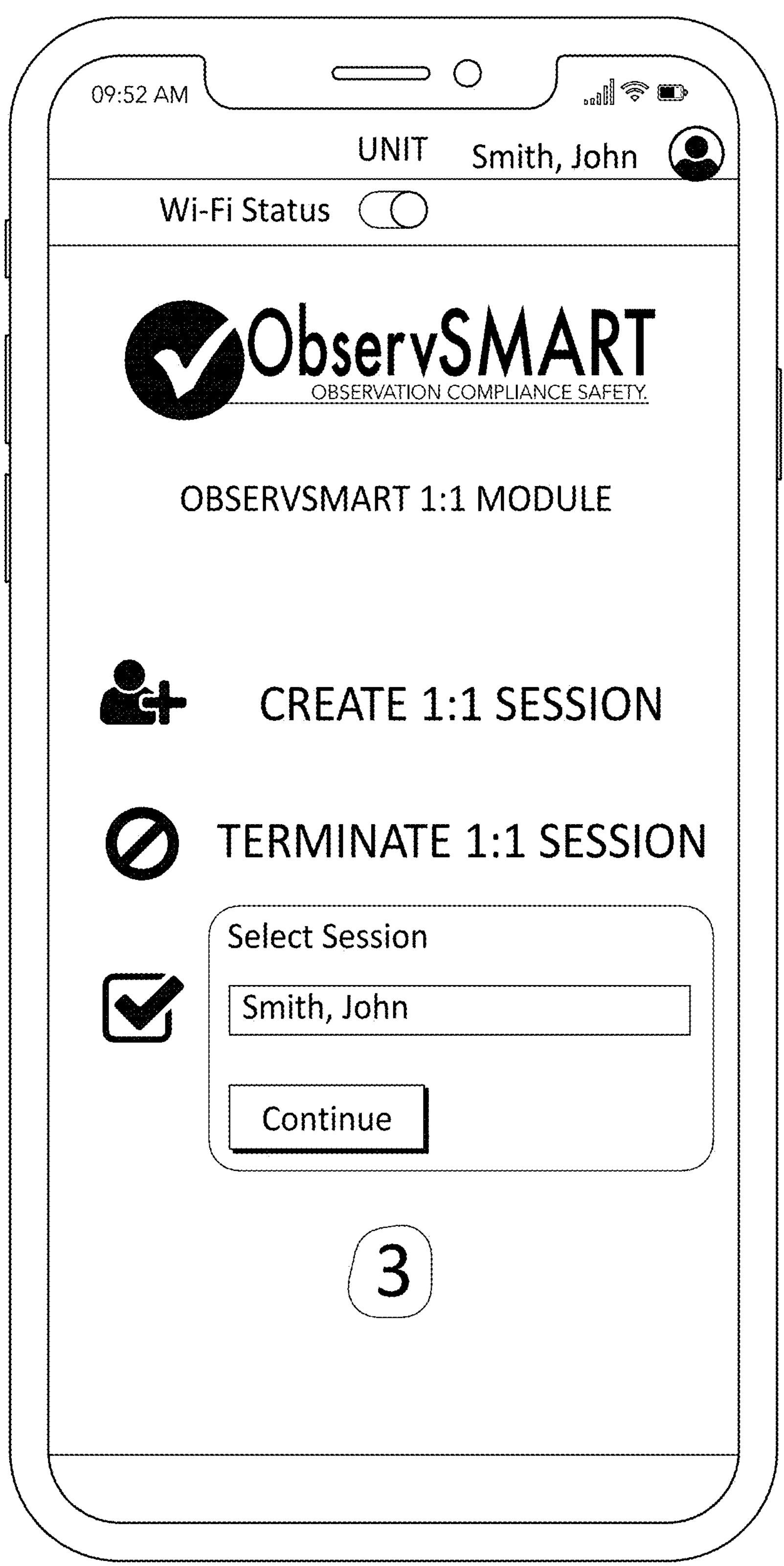
Figure 4D:
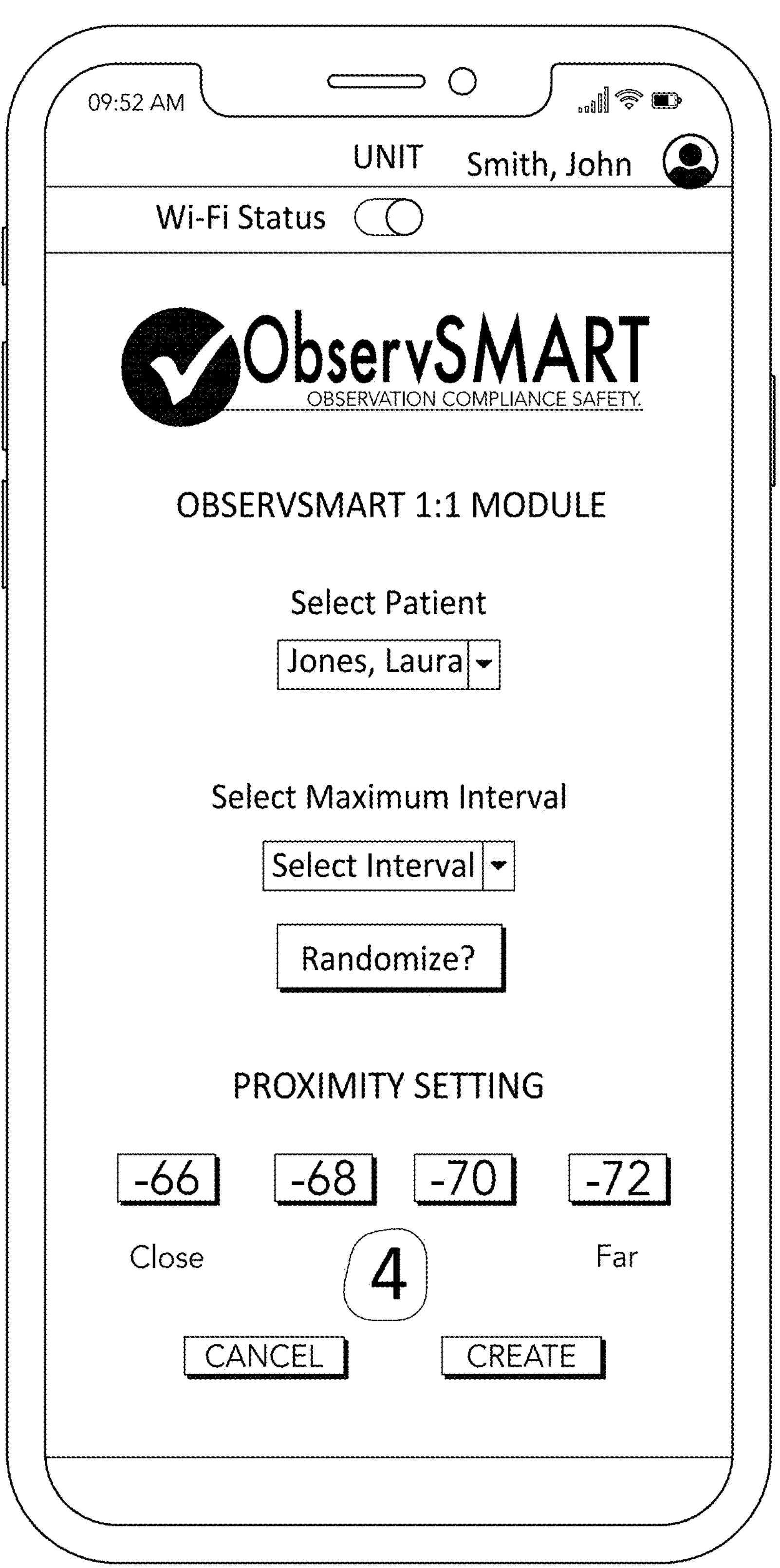

In FIG. 4B, the observer (user) may select which 'unit' (e.g., home unit) to observer. For example, the user may see all the home units and may select one. Only 1:1 sessions for subjects assigned to a particular home unit can be viewed and selected in this example. FIG. 4C shows an example of a user interface that may be seen and manipulated by an administrator. In FIG. 4C, the menu allows the administrator to create a session. The administrator will be able to create a session by selecting the subject (a subject can only be in one 1:1 session at a time), selecting an observation interval, selecting interval randomization, and selecting one of four preset proximity ranges (RSSI values), as shown in FIG. 4D. In this example, subjects can be selected from any subject on that particular home unit that is not already in a 1:1 session. A 1:1 session may not become active until the first time an observer logs in. Once a subject (patient) becomes active in a 1:1 session, an active session logout indication will appear on the home unit screen (e.g. FIG. 4D).

Figure 4E:
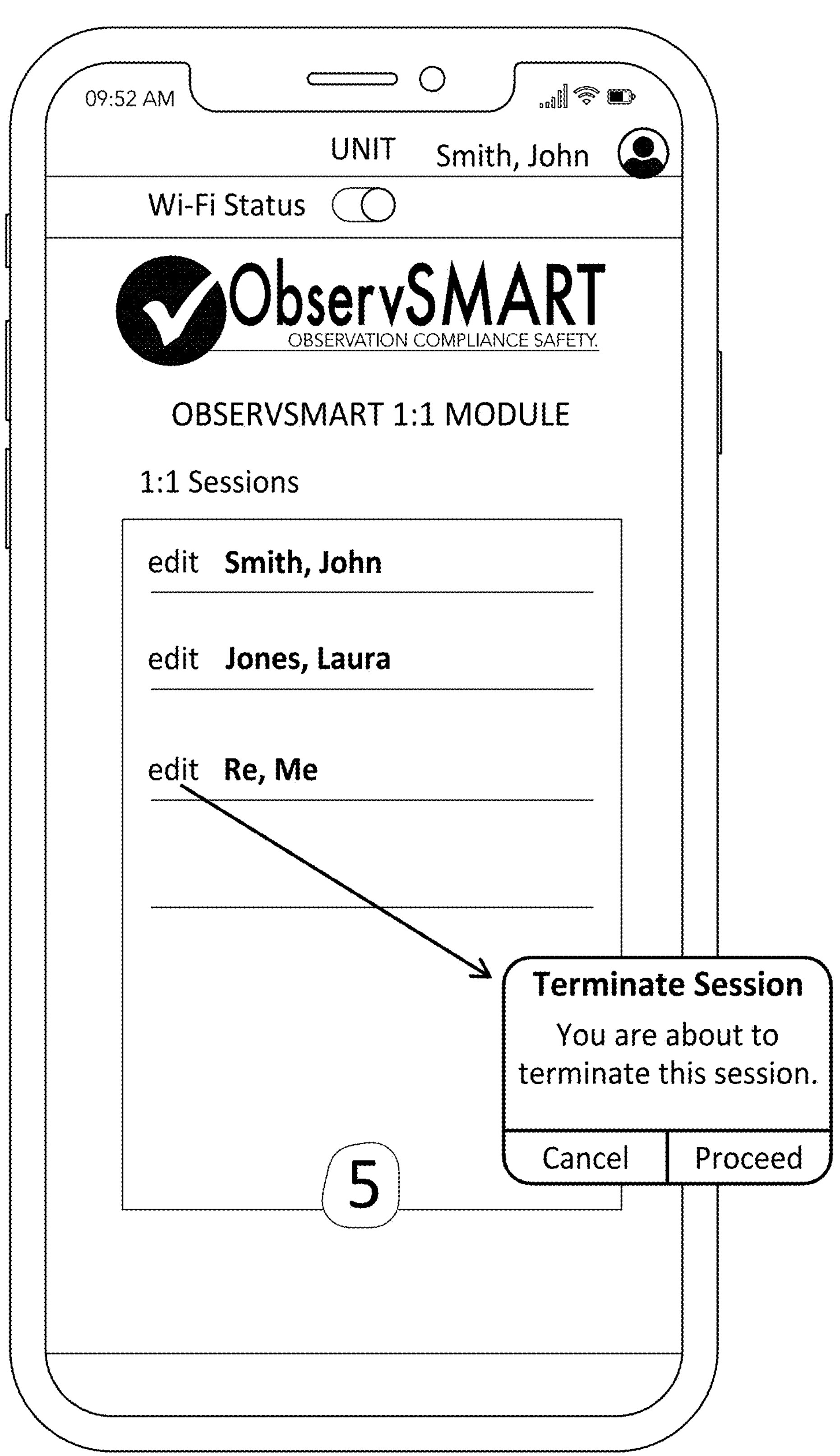

In this example, the observation interval may be setup during subject creation to specify an initial observation interval for the purposes of 1:1 observation. If randomization is selected, the control logic may prompt the observer to do observations for an interval randomized from, e.g., a minimum of 5 min to the nominal selected (e.g. 15 min). FIG. 4C illustrates the terminate/edit session controls on the user interface; an administrator may be able to terminate/edit a session by selecting the 'edit' link next to the session label, as shown in FIG. 4E (adjacent to the subject's name).

Selecting ‘edit’ may provide the option to terminate or edit the session (shown in FIG. 4D). Confirmation will be required to terminate a session.

Figure 4F:
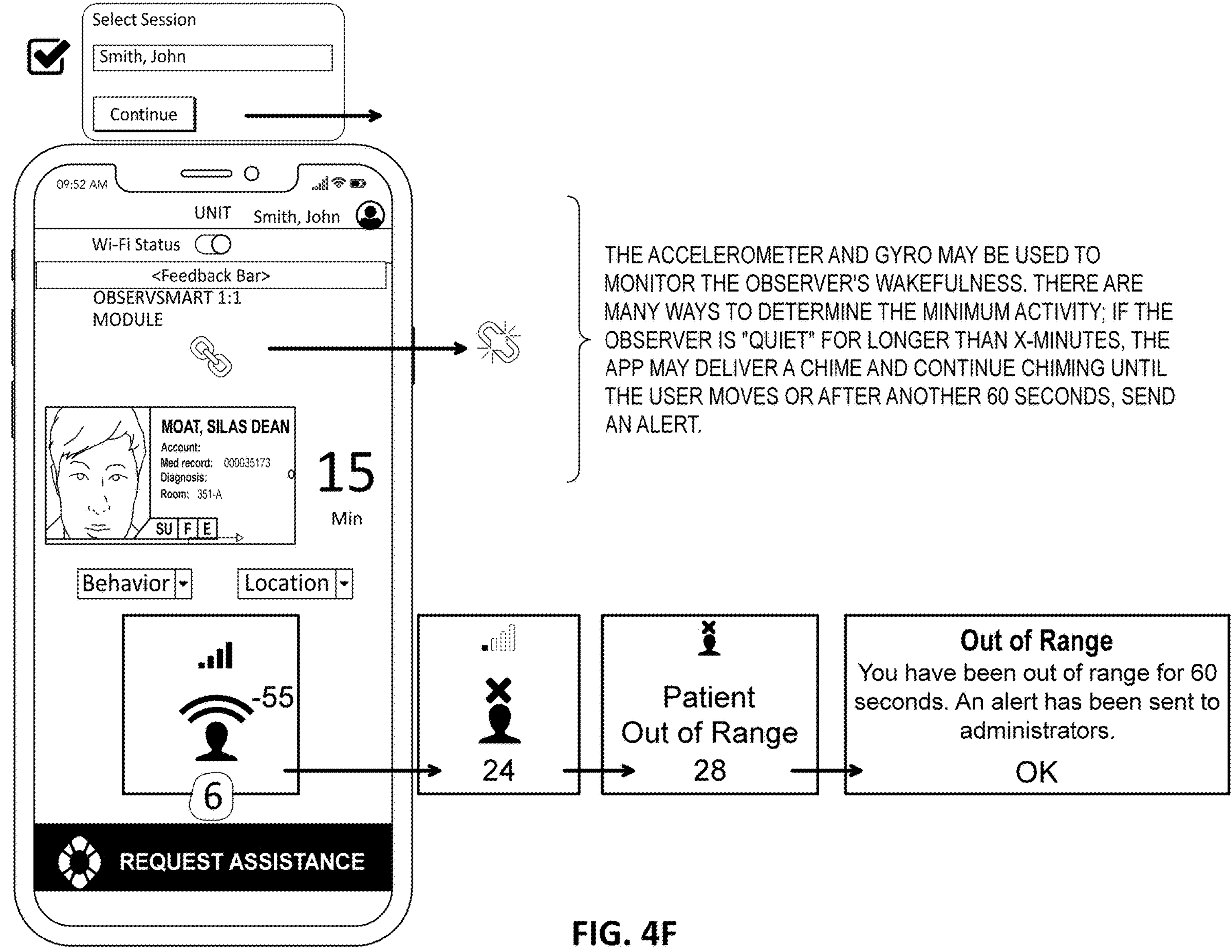

An observer may select a subject 1:1 session which will take them into the user interface screen shown in FIG. 4F. Once the observer enters a 1:1 session for the first time, the observer control logic may activate the session and trigger the change in subject status on a web and app screens, and may require at least one user to be logged in at all times until the session is terminated by an administrator.

FIG. 4F is an example of a user interface for the observer control during a period of active monitoring. In this example, the subject being observed is indicted, as is the proximity/range to the subject. A symbol (e.g., the “chain link” symbol shown in FIG. 4F or something similar) may be used to indicate that the user is “awake” and/or that the accelerometer/gyro is registering a threshold of activity for the observer device. The control logic may use two or more variables to determine if someone is “awake” or producing the minimum amount of movement, such as an accelerometer/gyroscope magnitude threshold and a time interval. If the control logic does not see at least one accelerometer/gyroscope threshold point within the time interval, the app will change the symbol (e.g., to a “broken link” or other symbol) and may alarm (e.g., chime) until the threshold is detected again. If a threshold activity signal is not hit within 60 seconds of the alarm initiating, an alert will be sent to the administrator. The alarm may continue until a threshold of activity is detected again. For example, an at-rest accelerometer reading threshold may be about 0.5%.

Figure 5:
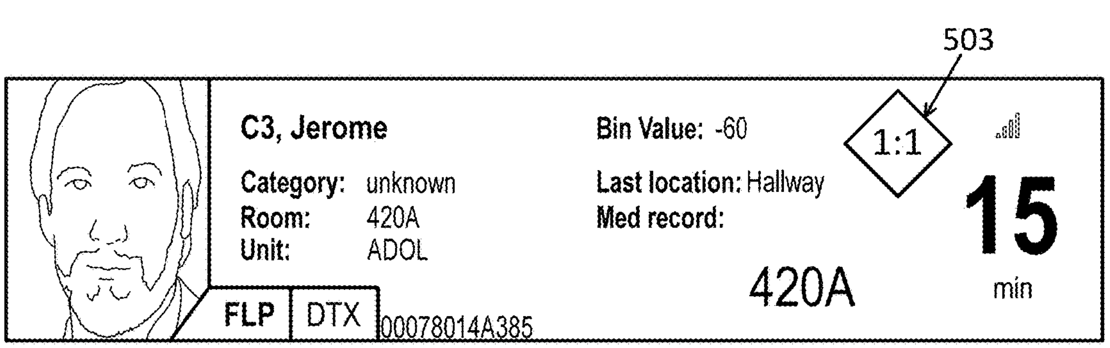
FIG. 5 is an enlarged detail or a portion of a user interface (similar to that shown in FIG. 4F) as described herein.

In any of these user interfaces, a subject information panel may be present that may include: a picture, name, MRN, room #, risk flags, and interval counter for the subject. An example of this is shown in FIG. 5. The user interface shown in FIG. 4F also includes behavior and location selection controls (e.g., wheels, pull-down menus, etc.). Observations may be done at the interval (or random interval) set during session creation. The subject panel behavior (e.g., range, out of range and forced behavior) may be included as shown diagrammatically in FIG. 4F.

As shown in FIG. 5, the user interface may include an indicator of the proximity as a bin value that is updated continuously; if the value drops below (e.g., out of range) of a threshold selected by the administrator (e.g., in FIG. 4D), the indicator may start a 30 second count-down. At 30 seconds, an out-of-range message maybe displayed which will trigger an alert after another 30 seconds or a total of 60 seconds elapsed from the time the bin value first dropped below the threshold. Once the alert pop-up appears, the alert escalation process may be reset, but the user may continue to use the app (the observation requests don’t stop regardless of the warnings).

As shown in the exemplary user interfaces, 1:1 sessions may be indicated on the home unit display of the web page and iPad app. When a 1:1 session is activated for a subject, their home unit status may change as shown in FIG. 5. A colored (e.g., yellow) diamond icon 503 with “1:1” in the center will appear on the iPad/web page display when a 1:1 session is activated. The symbol will disappear when the session is terminated. The presence of the symbol will not prevent a user from rounding on the subject.

Detecting Improper Patient Contact

In addition to the 1:1 monitoring described herein, in some variations these methods and apparatuses may be configured to monitor one or more patients indirectly, which may be particularly useful when rounding (1:1 monitoring) is not possible or is less frequent than otherwise desired.

As an additional and/or alternative portion of the methods and systems described herein, a system or method may include one or more static monitors or relays that may be positioned in or near a subject’s room in order to receive signals from patient-worn beacons. These signals may receive and/or transmit the unique beacon (and therefore patient) identifying code as mentioned above and/or other sensed data from the one or more patient-worn beacons, such as vital signs (e.g., heart rate, blood pressure, pulse oxygenation, temperature, etc.), movement (e.g., accelerometer data, etc.), etc. The received signals may be locally (e.g., at the static observer/monitor or relay) processed or remotely processed, including analyzing the data to detect or determine patient crisis (e.g., based on vitals and/or movement), proximity (e.g., patient moving out of range, or signal decreasing beyond range) or the like. The received signals may additionally or alternatively be transmitted to a remove observer (e.g., remote monitoring processor, which may be manned). In some variations the local monitor/observer may trigger one or more alarms, including alerting an observer that may be away from the subject.

For example, also described herein are methods of detecting unwanted or prohibited contact between subject’s wearing subject-worn beacons. In some cases, multiple subjects may be co-housed, including in the same room or nearby rooms. It may be desirable to detect (in order to prevent or limit) inappropriate or likely inappropriate interactions between patients, such as fighting or sexual congress. In some variations the subject-worn beacons may sense proximity relative to each other and may transmit this information to an observer device or other sensing/monitoring device (including static, such as wall-mounted observer devices, relays or links to remote monitoring and/or remote observer devices). This may be detected using RF energy (e.g., Bluetooth, etc.) or other means, from which distance may be triangulated or otherwise determined directly. However, in some variations it may be desirable, e.g., to extend or protect battery charge and/or life, to use subject-worn beacons that do not receive signals and/or that only transmit.

In some variations a method and/or system for performing the method may be configured to detect or approximate subject-to-subject interaction using motion data from each subject-worn beacon. These beacons may be configured for transmitting only (e.g., without receiving). Thus, the beacons may be configured to transmit a unique ID (e.g., corresponding to a particular associated subject) and movement data (e.g., from an accelerometer, etc.). For example, the movement data may be transmitted to a local or remote observer (such as an observer device worn by an observer, a relay in or near the patient’s room, a remote observe station receiving this data, etc.). During periods in which the subjects are to be sleeping (based, e.g., on the time of day or other subject schedule information, which may be included in the patient data described herein), if movement data indicates more than one subject, in the same or in some variations, adjacent, shows a higher level of activity (e.g., above a threshold level) then the system may trigger an alert indicating that improper contact between subject’s is likely occurring. The observer or other caregiver may receive the alert. In addition, this data may optionally be stored for later review. The threshold value may be configured to be greater than values for average sleep movement (e.g., rolling over, snoring, etc.). Further, the system or method may be configured to trigger the alert/alarm when the movement above threshold is concurrent within a particular time frame (e.g., within 30 seconds, within 1 minute, within 2 minutes, within 3 minutes, etc.). The movement value (from, e.g., an accelerometer) in the patient-worn beacon for each patient may be above the threshold, and may be transmitted to the observer or other monitoring device which may apply monitoring logic to confirm that it is within a sleeping time period for the subjects (e.g., between 9 μm and 7 am, between 10 μm and 7 am, etc., depending on institutional rules or guidance, which may be provided to the apparatus), and that the movement data (e.g., accelerometer data) is above threshold for each patient, and that the movement data is concurrent between two or more patients.

In some variations, the movement data of different subject-worn beacons may be compared, so that coordination of movements (e.g., similar large movements, frequencies of movements, etc.) is detected, e.g., above a threshold. Coordination of movements may also indicate that the subjects are interacting. Thus, in some variations the use of motion detection/sensing in patient-worn beacons may be used to detect interaction (as a surrogate for proximity between patient-worn beacons) between patients. The coordination of movement may be used at any time, even outside of normal sleeping periods, to indicate improper interaction between subjects.

In any of these examples, the methods and systems may also be provided with subject housing information, such as indicating when two or more subjects are housed together, e.g., in the same room, in the same hall, in the same floor, etc.

As mentioned, the beacons may transmit continuously or periodically (e.g., within every x seconds, every x minutes, etc. where x is 1, 2, 3, 4, 5, 6, 7, 8, 9, 10, etc.) on a regular or irregular schedule.

Figure 6:
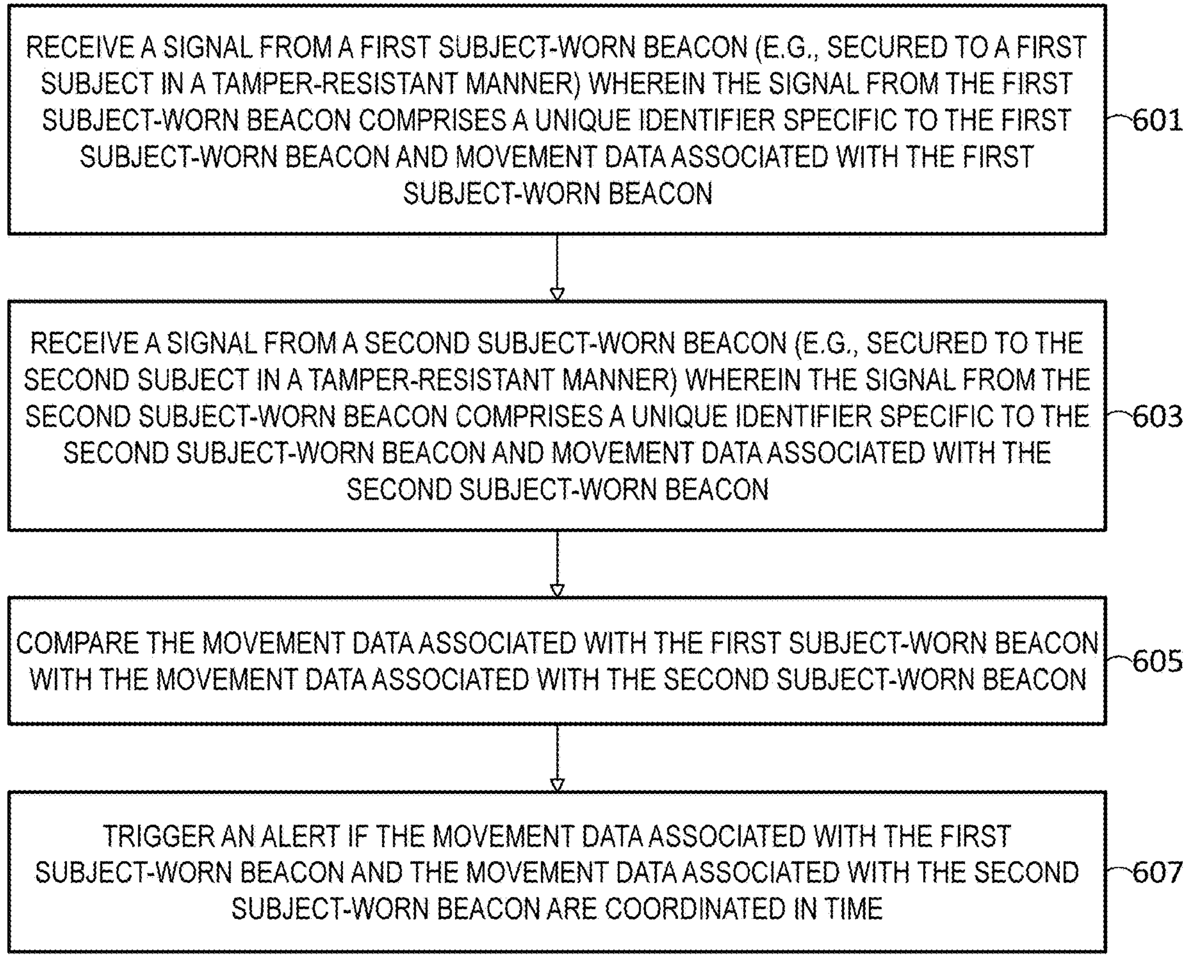
FIG. 6 illustrates one example of a method of detecting contact (e.g., improper contact) between subject as described herein.

For example, FIG. 6 illustrates one method of detecting contact (e.g., improper contact) between subject's wearing subject-worn beacons as descried herein. In FIG. 6, one example of a method is described. This method may be performed by an apparatus, such as an apparatus including a non-transitory computer-readable medium including contents that are configured to cause one or more processors to perform the method. As shown in FIG. 6, a signal may be received from a first subject-worn beacon (e.g., secured to a first subject in a tamper-resistant manner) wherein the signal from the first subject-worn beacon comprises a unique identifier specific to the first subject-worn beacon and movement data associated with the first subject-worn beacon 601. A signal may also be received from a second subject-worn beacon (e.g., secured to the second subject in a tamper-resistant manner) wherein the signal from the second subject-worn beacon comprises a unique identifier specific to the second subject-worn beacon and movement data associated with the second subject-worn beacon 603. The method or apparatus may then compare the movement data associated with the first subject-worn beacon with the movement data associated with the second subject-worn beacon 605, and may trigger an alert if the movement data associated with the first subject-worn beacon and the movement data associated with the second subject-worn beacon are coordinated in time 607.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of close-proximity monitoring of a subject, the method comprising:
- logging in a first observer for line-of-sight monitoring of a subject, wherein the line-of site monitoring includes:
  - receiving a signal from a subject-worn beacon;
  - determining a proximity between the subject and the first observer from the signal;
  - prompting the first observer to record a subject observation at an interval of 15 minutes or less; and
  - emitting one or more alerts when one or more of: the first observer is further than a predetermined range from the subject; and the first observer does not record a subject observation within a predetermined observation time;
- logging in a second observer for line-of-sight monitoring of the subject; and
- logging the first observer out of line-of-sign monitoring only after the second observer has been logged in.

2. The method of claim 1, wherein logging in the first observer comprises logging in the first observer into an automated monitoring system.

3. The method of claim 1, wherein logging in the first observer comprises selecting the subject from a list of subjects.

4. The method of claim 1, wherein receiving the signal from the subject-worn beacon comprises receiving the signal from a subject-worn beacon that is secured to a subject so that it cannot be removed by the subject.

5. The method of claim 1, wherein prompting the first observer comprises prompting the first observer at a random time interval of between 1 minute and 15 minutes.

6. The method of claim 1, further comprising confirming that the first observer is awake and wherein emitting one or more alerts from an observer device further comprising emitting the one or more alerts when the first observer is not awake.

7. The method of claim 1, further comprising confirming that the first observer is awake based on an activity level measured from an observer device and wherein emitting one or more alerts from the observer device further comprising emitting the one or more alerts when the first observer is not awake.

8. The method of claim 1, wherein emitting one or more alerts from an observer device comprises emitting one or more alerts from the observer device when one or more of: the first observer is further than a predetermined range from the subject for greater than a predetermined time interval.

9. The method of claim 1, further comprising transmitting a report to a supervisor if the first observer does not comply with the one or more alerts within a compliance time period.

10. The method of claim 1, wherein emitting one or more alerts from an observer device comprises emitting one or more of: an audible alert, a tactile alert, and a visual alert.

11. The method of claim 1, wherein the signal is transmitted from the subject-worn beacon with a periodic frequency 0.01 Hz or greater.

12. A system for close-proximity monitoring subjects, the system comprising:

a subject-worn beacon, wherein the subject-worn beacon is configured to wirelessly transmit a signal and further wherein the subject-worn beacon comprises a tamper-resistant latch that is configured to secured to the subject-worn beacon to the subject so that the subject-worn beacon cannot be removed by the subject;

a memory comprising computer-program instructions, that, when executed by one or more processors of a wearable observer device, perform a computer-implemented method comprising:

receiving the signal in the wearable observer device;

determining a proximity between the subject and an observer from the signal;

prompting the observer to record a subject observation at an interval of 15 minutes or less; and emitting one or more alerts from the observer device when one or more of: the observer is further than a predetermined range from the subject; and the observer does not record a subject observation within a predetermined observation time.

13. The system of claim 12, wherein the computer-implemented method step of prompting the observer comprises prompting the observer at an interval of 10 minutes or less.

14. The system of claim 12, further wherein the computer-implemented method further comprises confirming that the observer is awake and wherein emitting one or more alerts from the observer device further comprising emitting the one or more alerts when the observer is not awake.

15. The system of claim 12, further wherein the computer-implemented method further comprises confirming that the observer is awake based on an activity level measured from the observer device and wherein emitting one or more alerts from the observer device further comprising emitting the one or more alerts when the observer is not awake.

16. The system of claim 12, wherein the predetermined range is 10 feet or greater.

17. The system of claim 12, wherein the computer-implemented method step of emitting one or more alerts from the observer device comprises emitting one or more alerts from the observer device when one or more of: the observer is further than a predetermined range from the subject for greater than a predetermined time interval.

18. The system of claim 12, further wherein the computer-implemented method further comprises transmitting a report to a supervisor if the observer does not comply with the one or more alerts within a compliance time period.

19. The system of claim 12, wherein the computer-implemented method step of emitting one or more alerts from the observer device comprises emitting one or more of: an audible alert, a tactile alert, and a visual alert.

20. The system of claim 12, wherein the signal is transmitted from the subject-worn beacon with a periodic frequency 0.01 Hz or greater.

* * * * *